(12) United States Patent
Mitchell et al.

(10) Patent No.: US 7,777,040 B2
(45) Date of Patent: Aug. 17, 2010

(54) CERTAIN SUBSTITUTED UREAS, AS MODULATORS OF KINASE ACTIVITY

(75) Inventors: Scott A. Mitchell, East Haven, CT (US); Mihaela Diana Danca, Mendham, NJ (US); Peter A. Blomgren, North Branford, CT (US); David R. Brittelli, Branford, CT (US); Pavel Zhichkin, Latham, NY (US); Matthew E. Voss, Nassau, NY (US)

(73) Assignee: CGI Pharmaceuticals, Inc., Branford, CT (US)

( * ) Notice: Subject to any disclaimer, the term of this patent is extended or adjusted under 35 U.S.C. 154(b) by 1142 days.

(21) Appl. No.: 11/415,419

(22) Filed: May 2, 2006

(65) Prior Publication Data

US 2006/0270702 A1    Nov. 30, 2006

Related U.S. Application Data

(60) Provisional application No. 60/677,758, filed on May 3, 2005, provisional application No. 60/677,530, filed on May 3, 2005.

(51) Int. Cl.
*C07D 215/38*    (2006.01)
(52) U.S. Cl. ..................................... 546/167
(58) Field of Classification Search ................. 546/159, 546/167
See application file for complete search history.

(56) References Cited

U.S. PATENT DOCUMENTS

| | | | |
|---|---|---|---|
| 4,301,169 A | 11/1981 | Yamanaka et al. | |
| 5,028,605 A | 7/1991 | Sablayrolles et al. | |
| 5,395,817 A | 3/1995 | Pallos et al. | |
| 5,508,288 A | 4/1996 | Forbes et al. | |
| 5,593,997 A | 1/1997 | Dow et al. | |
| 5,658,857 A | 8/1997 | Andree et al. | |
| 5,783,576 A | 7/1998 | Roos et al. | |
| 6,344,465 B1 | 2/2002 | Armistead et al. | |
| 6,541,496 B1 | 4/2003 | Armistead et al. | |
| 6,627,647 B1 | 9/2003 | Betageri | |
| 6,645,990 B2 | 11/2003 | Askew et al. | |
| 6,720,427 B2 * | 4/2004 | Sanner et al. ............... 548/193 |
| 6,919,340 B2 | 7/2005 | Paruch et al. | |
| 6,919,341 B2 | 7/2005 | Paruch et al. | |
| 6,933,316 B2 | 8/2005 | Hsieh et al. | |
| 7,160,885 B2 | 1/2007 | Currie et al. | |
| 7,189,723 B2 | 3/2007 | Mitchell et al. | |
| 7,259,164 B2 | 8/2007 | Mitchell et al. | |
| 7,312,341 B2 | 12/2007 | DeSimone et al. | |
| 2002/0103138 A1 | 8/2002 | D'Andrea et al. | |
| 2003/0181482 A1 | 9/2003 | Chen et al. | |
| 2003/0195244 A1 | 10/2003 | Hsieh et al. | |
| 2003/0212073 A1 | 11/2003 | Currie et al. | |
| 2004/0063715 A1 | 4/2004 | Paruch et al. | |
| 2004/0067951 A1 | 4/2004 | DeSimone et al. | |
| 2004/0072835 A1 | 4/2004 | Paruch et al. | |
| 2004/0198733 A1 | 10/2004 | Schwink et al. | |
| 2004/0220189 A1 | 11/2004 | Sun et al. | |
| 2004/0235892 A1 | 11/2004 | Dai et al. | |
| 2005/0009832 A1 | 1/2005 | Sun et al. | |
| 2005/0038069 A1 | 2/2005 | Cox et al. | |
| 2005/0054648 A1 | 3/2005 | Mitchell et al. | |
| 2005/0054649 A1 | 3/2005 | Currie et al. | |
| 2005/0085484 A1 | 4/2005 | Mitchell et al. | |
| 2005/0090499 A1 | 4/2005 | Currie et al. | |
| 2005/0101604 A1 | 5/2005 | Currie et al. | |
| 2005/0124620 A1 | 6/2005 | Frederickson et al. | |
| 2005/0267108 A1 | 12/2005 | Hsieh et al. | |
| 2005/0288295 A1 | 12/2005 | Currie et al. | |
| 2006/0183746 A1 | 8/2006 | Currie et al. | |
| 2006/0199846 A1 | 9/2006 | Mitchell et al. | |
| 2006/0211738 A1 | 9/2006 | Mitchell et al. | |

FOREIGN PATENT DOCUMENTS

DE    04337609    5/1995

(Continued)

OTHER PUBLICATIONS

International Search Report and Written Opinion mailed Apr. 17, 2007, for international application No. PCT/US2006/016916, filed May 2, 2006.
De Lucca et al., 2002, "Discovery and Structure—Activity Relationship of N-(Ureidoalkyl)-Benzyl-Piperidines As Potent Small Molecule CC Chemokine Receptor-3 (CCR3) Antagonists," J. Med. Chem., 45: 3794-3804.

(Continued)

*Primary Examiner*—D. Margaret Seaman
(74) *Attorney, Agent, or Firm*—Finnegan Henderson Farabow Garrett & Dunner LLP

(57) ABSTRACT

Certain chemical entities chosen from compounds of Formula 1 and pharmaceutically acceptable salts, solvates, chelates, non-covalent complexes, and prodrugs thereof, are provided herein. Pharmaceutical compositions comprising at least one chemical entity and one or more pharmaceutically acceptable vehicles chosen from carriers, adjuvants, and excipients, are also provided herein. Methods of treating patients suffering from certain diseases and disorders responsive to angiogenic kinase modulation, which comprise administering to such patients an amount of at least one chemical entity effective to reduce signs or symptoms of the disease or disorder are disclosed. These diseases include cancer, including breast neoplasia, endometrial cancer, colon cancer, and neck squamous cell carcinoma. Methods of treatment include administering at least one chemical entity as a single active agent or administering such at least one chemical entity in combination with one or more other therapeutic agents. A method for determining the presence or absence of an angiogenic kinase in a sample comprising contacting the sample with at least one chemical entity under conditions that permit detection of activity of the angiogenic kinase, detecting a level of the activity of the angiogenic kinase, and therefrom determining the presence or absence of the angiogenic kinase in the sample.

30 Claims, No Drawings

FOREIGN PATENT DOCUMENTS

| | | |
|---|---|---|
| EP | 0480713 A1 | 4/1992 |
| EP | 0 535 923 A1 | 4/1993 |
| EP | 0 535 924 A1 | 4/1993 |
| EP | 0 535 925 A1 | 4/1993 |
| EP | 0 535 926 A1 | 4/1993 |
| EP | 0 535 925 B1 | 4/1996 |
| EP | 1 170 288 B1 | 1/2002 |
| WO | WO 88/04298 A1 | 6/1988 |
| WO | WO 89/09212 A1 | 10/1989 |
| WO | WO 93/15049 A1 | 8/1993 |
| WO | WO 95/12594 A1 | 5/1995 |
| WO | WO 96/04298 A1 | 2/1996 |
| WO | WO 96/34866 A1 | 11/1996 |
| WO | WO 96/39382 A1 | 12/1996 |
| WO | WO 96/40673 A1 | 12/1996 |
| WO | WO 98/24785 A1 | 6/1998 |
| WO | WO 98/47868 A1 | 10/1998 |
| WO | WO 98/50346 A2 | 11/1998 |
| WO | WO 99/28322 A1 | 6/1999 |
| WO | WO 99/32106 A1 | 7/1999 |
| WO | WO 99/32436 A1 | 7/1999 |
| WO | WO 99/43651 A2 | 9/1999 |
| WO | WO 99/43654 A2 | 9/1999 |
| WO | WO 00/24707 A1 | 5/2000 |
| WO | WO 00/64872 A2 | 11/2000 |
| WO | WO 01/00657 A2 | 1/2001 |
| WO | WO 01/27119 A2 | 4/2001 |
| WO | WO-01/58893 A2 | 8/2001 |
| WO | WO 02/10170 A1 | 2/2002 |
| WO | WO 02/30428 A1 | 4/2002 |
| WO | WO 02/060492 A1 | 8/2002 |
| WO | WO 02/066481 A1 | 8/2002 |
| WO | WO 02/076985 A1 | 10/2002 |
| WO | WO 03/024447 A1 | 3/2003 |
| WO | WO 03/037887 A1 | 5/2003 |
| WO | WO 03/070732 A1 | 8/2003 |
| WO | WO 03/072541 A2 | 9/2003 |
| WO | WO 03/087087 A2 | 10/2003 |
| WO | WO 03/099771 A2 | 12/2003 |
| WO | WO 2004/026310 A1 | 4/2004 |
| WO | WO 2004/026877 A1 | 4/2004 |
| WO | WO 2004/056830 A1 | 7/2004 |
| WO | WO 2004/080979 A1 | 9/2004 |
| WO | WO 2004/085425 A1 | 10/2004 |
| WO | WO 2004/100947 A2 | 11/2004 |
| WO | 2004113352 * | 12/2004 |
| WO | WO 2005/097755 A2 | 10/2005 |
| WO | WO 2006/030031 A1 | 3/2006 |
| WO | WO-2006/053342 A2 | 5/2006 |

OTHER PUBLICATIONS

Ding et al. (2002) "A Combinatorial Scaffold Approach toward Kinase-Directed Heterocycle Libraries," J. Am. Chem. Soc., 124(8): 1594-1596.
Fabian et al. (2005) "A small molecule-kinase interaction map for clinical kinase inhibitors," Nature Biotechnology 23(3): 329-336.
Hanks (Apr. 1, 1994) "Hanks Classification: Protein Kinase Classification, provided by Steven K. Hanks," pp. 1-4, from http://pkr.sdsc.edu/html/pk_classification/pk_catalytic/pk_hanks_class.html.
Human Kinome poster (2002) Science (accompanies Manning et al. 2002 "The Protein Kinase Complement of the Human Genome," Science 298(5600) 1912-1916, 1933-1934—see cite C9).
Jeffrey et al. (1998) "Phosphodiesterase III and V Inhibitors on Pulmonary Artery from Pulmonary Hypertensive Rats: Differences Between Early and Established Pulmonary Hypertension," J. Cardiovascular Pharmacology, 32:213-219.
Kulkarni et al. (1969) Journal of Pharmaceutical Sciences 58(7), pp. 852-857.
Lumma Jr. et al. (1983) "Piperazinylimidazo[1,2-a]pyrazines with Selective Affinity for in Vitro alpha-Adrenergic Receptor Subtypes," J. Med. Chem., 26:357-363.
Manning et al. (2002) "The Protein Kinase Complement of the Human Genome," Science 298(5600) 1912-1916, 1933-1934.
"Protein Kinases in Disease," references produced from a Sep. 24, 1997, search of the On-line Meddelian Inheritance in Man (OMIM) database, pp. 1-11, from http://bioinformatics.weizmann.ac.il/Kinases/pkr/pk_medicine.html.
Stenberg et al. (2000) "KinMutBase, a database of human disease-causing protein kinase mutations," Nucleic Acids Research, 28(1):369-371.
Vitse et al. (1999) "New Imidazo[1,2-a]pyrazine Derivatives with Brochodilatory and Cyclic Nucleotide Phosphodiesterase Inhibitory Activities," Bioorganic & Medicinal Chemistry, 7: 1059-1065.
International Search Report dated Oct. 22, 2003, for Application No. PCT/US03/12222, International filing date Apr. 21, 2003.
Written Opinion dated Dec. 5, 2003, for Application No. PCT/US03/12222, International filing date Apr. 21, 2003.
Second Written Opinion dated Apr. 13, 2004, for Application No. PCT/US03/12222, International filing date Apr. 21, 2003.
International Preliminary Examination Report dated Aug. 3, 2004, for Application No. PCT/US03/12222, International filing date Apr. 21, 2003.
International Search Report dated Feb. 9, 2004, for Application No. PCT/US03/28329, International filing date Sep. 9, 2003.
Written Opinion dated Jul. 6, 2004, for Application No. PCT/US03/28329, International filing date Sep. 9, 2003.
International Preliminary Examination Report dated Oct. 27, 2004, for Application No. PCT/US03/28329, International filing date Sep. 9, 2003.
International Search Report and Written Opinion dated Jul. 7, 2004, for Application No. PCT/US2004/003922, International filing date Feb. 10, 2004.
International Search Report and Written Opinion dated Jul. 7, 2004, for Application No. PCT/US2004/003923, International filing date Feb. 10, 2004.
International Search Report and Written Opinion dated Dec. 30, 2004, for Application No. PCT/US2004/018227, International filing date Jun. 4, 2004.
International Search Report and Written Opinion dated Dec. 8, 2004, for Application No. PCT/US2004/021150, International filing date Jun. 30, 2004.
International Search Report and Written Opinion dated Feb. 1, 2005, for Application No. PCT/US2004/025884, International filing date Aug. 11, 2004.
International Search Report and Written Opinion dated Jun. 23, 2005, for Application No. PCT/US2004/037433, International filing date Nov. 10, 2004.
International Search Report and Written Opinion dated May 26, 2006, for Application No. PCT/US2006/001271, International filing date Jan. 13, 2006.
International Search Report and Written Opinion dated May 26, 2006 for Application No. PCT/US2006/001272, international filing date Jan. 13, 2006.
Office Action dated Sep. 26, 2006, for U.S. Appl. No. 10/658,121, filed Sep. 9, 2003.
Notice of Allowance dated Mar. 6, 2007 for U.S. Appl. No. 10/658,121, filed Sep. 9, 2003.
Notice of Allowance dated Aug. 8, 2007 for U.S. Appl. No. 10/658,121, filed Sep. 9, 2003.
Office Action dated Jan. 8, 2007, for U.S. Appl. No. 10/915,696, filed Aug. 11, 2004.
Office Action dated Feb. 11, 2009, for U.S. Appl. No. 11/331,347, filed Jan. 13, 2006.
Restriction Requirement dated Oct. 20, 2004, for U.S. Appl. No. 10/419,682, filed Apr. 21, 2003.
Notice of Allowance dated Feb. 8, 2005, for U.S. Appl. No. 10/419,682, filed Apr. 21, 2003.
Office Action dated Apr. 3, 2006, for U.S. Appl. No. 10/776,002, filed Feb. 10, 2004.
Notice of Allowance dated Aug. 11, 2006, for U.S. Appl. No. 10/776,002, filed Feb. 10, 2004.

Office action dated May 24, 2006, for U.S. Appl. No. 10/776,631, filed Feb. 10, 2004.

Notice of Allowance dated Sep. 7, 2006, for U.S. Appl. No. 10/776,631, filed Feb. 10, 2004.

Office Action dated Jul. 6, 2007, for U.S. Appl. No. 10/861,791, filed Jun. 4, 2004.

Office Action dated Sep. 29, 2006, for U.S. Appl. No. 10/861,791, filed Jun. 4, 2004.

Notice of Allowance dated Mar. 19, 2008, for U.S. Appl. No. 10/861,791, filed Jun. 4, 2004.

Supplemental Notice of Allowance dated May 22, 2008, for U.S. Appl. No. 10/861,791, filed Jun. 4, 2004.

Office Action dated Sep. 19, 2006, for U.S. Appl. No. 10/883,646, filed Jun. 30, 2004.

Office Action dated Jun. 18, 2007, for U.S. Appl. No. 10/883,646, filed Jun. 30, 2004.

Notice of Allowance dated Dec. 27, 2007, for U.S. Appl. No. 10/883,646, filed Jun. 30, 2004.

Office Action dated Apr. 10, 2009 for U.S. Appl. No. 11/331,346, filed Jan. 13, 2006.

* cited by examiner

CERTAIN SUBSTITUTED UREAS, AS MODULATORS OF KINASE ACTIVITY

This application claims priority to U.S. Application No. 60/677,758, filed May 3, 2005; and Application No. 60/677,530, filed May 3, 2005, each of which is incorporated herein by reference.

Provided herein are certain substituted ureas and related compounds, compositions comprising such compounds, and methods of their use.

Protein kinases, the largest family of human enzymes, encompass well over 500 proteins. Kinases play a key role in angiogenesis. Angiogenesis, the formation of new blood vessels from preexisting ones, plays a significant role in many pathological settings, including cancer, chronic inflammation, diabetic retinopathy, psoriasis, rheumatoid arthritis, and macular degeneration. Anti-angiogenic therapy represents a potentially important approach for the treatment of solid tumors and other diseases associated with dysregulated vascularization.

The process of angiogenesis is complex, requiring the concerted actions of multiple angiogenic mediators as well as the participation of different cell types. Key angiogenesis mediators, including, VEGF, FGF, and angiopoietin 1 and 2 (Ang1 and Ang2) that bind to their cognate receptors (VEGFRs, FGFRs and Tie1 and Tie2, respectively) expressed on endothelial cells, as well as platelet-derived growth factor (PDGF) that binds to its receptor (PDGFRα) expressed on VEGF-producing stromal cells or its receptor (PDGFRβ) expressed on pericytes and smooth muscle cells have been identified. Recent studies indicate that several members of the ephrin family and their receptor Eph family are also regulators of angiogenesis. VEGFRs, FGFRs, Tie1, Tie2, PDGFRs, and Eph receptors all belong to the receptor protein tyrosine kinase (RTK) superfamily. Given the important roles of these RTKs in angiogenesis, their modulation would be pharmacologically desirable for the treatment of cancer and other disease.

Provided is at least one chemical entity chosen from compounds of Formula 1

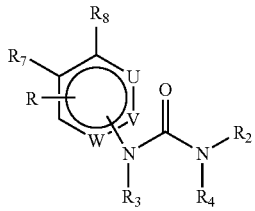

(Formula 1)

and pharmaceutically acceptable salts, solvates, chelates, non-covalent complexes, and prodrugs, wherein U, V, and W are chosen from CH and N, provided that no more than two of U, V, and W are N;

R represents 0 to 2 substituents independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, sulfanyl, sulfinyl, sulfonyl, optionally substituted aryl, optionally substituted heteroaryl, and optionally substituted heterocycloalkyl;

$R_7$ and $R_8$, taken together with the carbons to which they are bound, form a fused 5- to 7-membered ring chosen from fused 5- to 7-membered cycloalkyl rings, fused 5- to 7-membered heteroaryl rings and fused 5- to 7-membered heterocyclic rings, wherein the fused 5- to 7-membered ring is substituted with a group —$(Z_1)_m R_1$ wherein $R_1$ is chosen from optionally substituted aryl and optionally substituted heteroaryl;

$Z_1$ is —$CR_5R_6$— wherein each $R_5$ and $R_6$ is independently chosen from hydrogen, optionally substituted $C_1$-$C_6$ alkyl, and halo; and m is chosen from 0, 1, and 2;

$R_2$ is optionally substituted aryl; and $R_3$ and $R_4$ are each independently chosen from hydrogen, optionally substituted $C_1$-$C_6$ alkyl, optionally substituted aryl, and optionally substituted heteroaryl, provided that when $R_7$ and $R_8$, taken together with the carbons to which they are bound, form a fused 5- to 7-membered ring other than a fused 4,5-dihydro-1H-imidazole ring, then at least one of U, V, and W is nitrogen.

Also provided is a pharmaceutical composition, comprising at least one chemical entity described herein, together with at least one pharmaceutically acceptable vehicle chosen from carriers, adjuvants, and excipients.

Also provided is a packaged pharmaceutical composition, comprising the pharmaceutical composition described herein in a container; and instructions for using the composition to treat a patient suffering from a disease or disorder responsive to kinase activity modulation of one or more tyrosine kinase.

Also provided is a method of treating a patient having a disease or disorder responsive to kinase activity modulation comprising administering to the patient a therapeutically effective amount of at least one chemical entity described herein or a pharmaceutical composition described herein.

Also provided is a method of modulating $EphB_4$ kinase activity, the method comprising contacting cells expressing $EphB_4$ with at least one chemical entity described herein in an amount sufficient to detectably inhibit $EphB_4$ kinase activity in vitro.

Also provided is a method of modulating VEGFR2 kinase activity, the method comprising contacting cells expressing VEGFR2 with at least one chemical entity described herein in an amount sufficient to detectably inhibit VEGFR2 kinase activity in vitro.

Also described is a method of modulating c-Kit kinase activity, the method comprising contacting cells expressing c-Kit with at least one chemical entity described herein in an amount sufficient to detectably inhibit c-Kit kinase activity in vitro.

Also provided is a method of modulating PDGFRβ kinase activity, the method comprising contacting cells expressing PDGFRβ with at least one chemical entity described herein in an amount sufficient to detectably inhibit PDGFRβ kinase activity in vitro.

Also provided is a method of modulating an activity of at least one kinase chosen from VEGFR2, $EphB_4$, PDGFRβ, and c-Kit, the method comprising contacting cells expressing at least one kinase chosen from VEGFR2, $EphB_4$, PDGFRβ, and c-Kit with at least one chemical entity described herein in an amount sufficient to detectably inhibit the activity of at least one kinase chosen from VEGFR2, $EphB_4$, PDGFRβ, and c-Kit in vitro.

Also described is the use of at least one chemical entity for the manufacture of a medicament for the treatment of a patient having a disease responsive to inhibition of at least one kinase chosen from VEGFR2, $EphB_4$, PDGFRβ, and c-Kit, wherein the at least one chemical entity is a chemical entity described herein.

Also described is a method for the manufacture of a medicament for the treatment of a patient having a disease responsive to inhibition of at least one kinase chosen from VEGFR2, EphB$_4$, PDGFRβ, and c-Kit, comprising including in said medicament at least one chemical entity described herein.

Also described is a method for determining the presence of an angiogenic kinase in a sample, comprising contacting the sample with at least one chemical entity described herein under conditions that permit detection of an activity of the angiogenic kinase, detecting a level of the activity of the angiogenic kinase in the sample, and therefrom determining the presence or absence of the angiogenic kinase in the sample.

As used in the present specification, the following words and phrases are generally intended to have the meanings as set forth below, except to the extent that the context in which they are used indicates otherwise. The following abbreviations and terms have the indicated meanings throughout:

Formula 1 includes all subformulae thereof. For example Formula 1 includes compounds of Formulae 2 to 9.

As used herein, when any variable occurs more than one time in a chemical formula, its definition on each occurrence is independent of its definition at every other occurrence. In accordance with the usual meaning of "a" and "the" in patents, reference, for example, to "a" kinase or "the" kinase is inclusive of one or more kinases.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example, 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to four carbons.

"Cycloalkyl" indicates a saturated or unsaturated hydrocarbon ring group, having the specified number of carbon atoms, usually from 3 to 7 ring carbon atoms, provided that the ring is not aromatic. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

"Mono- and di-alkylcarboxamide" encompasses a group of the formula —(C═O)NR$_a$R$_b$ where R$_a$ and R$_b$ are independently chosen from hydrogen and alkyl groups of the indicated number of carbon atoms, provided that R$_a$ and R$_b$ are not both hydrogen.

By "alkylthio" is meant an alkyl group of the indicated number of carbon atoms attached through a sulfur bridge.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula CH$_3$(C═O)—.

By "alkoxycarbonyl" is meant an ester group of the formula (alkoxy)(C═O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

By "amino" is meant the group —NH$_2$.

"Mono- and di-(alkyl)amino" encompasses secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propylamino.

"Mono- and di-(alkyl)aminoalkyl" encompasses mono- and di-(alkyl)amino as defined above linked to an alkyl group.

By "amino(alkyl)" is meant an amino group linked to an alkyl group having the indicated number of carbons. Similarly "hydroxyalkyl" is a hydroxy group linked to an alkyl group.

The term "aminocarbonyl" refers to the group —CONR$^b$R$^c$, where

R$^b$ is chosen from H, optionally substituted $C_1$-$C_6$ alkyl, optionally substituted aryl, and optionally substituted heteroaryl; and R$^c$ is chosen from hydrogen and optionally substituted $C_1$-$C_4$ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —OC$_1$-$C_4$ alkyl, —OC$_1$-$C_4$ alkylphenyl, —C$_1$-$C_4$ alkyl-OH, —OC$_1$-$C_4$ haloalkyl, halo, —OH, —NH$_2$, —C$_1$-$C_4$ alkyl-NH$_2$, —N(C$_1$-$C_4$ alkyl)(C$_1$-$C_4$ alkyl), —NH(C$_1$-$C_4$ alkyl), —N(C$_1$-$C_4$ alkyl)(C$_1$-$C_4$ alkylphenyl), —NH(C$_1$-$C_4$ alkylphenyl), cyano, nitro, oxo (as a substitutent for heteroaryl), —CO$_2$H, —C(O)OC$_1$-$C_4$ alkyl, —CON(C$_1$-$C_4$ alkyl)(C$_1$-$C_4$ alkyl), —CONH(C$_1$-$C_4$ alkyl), —CONH$_2$, —NHC(O)(C$_1$-$C_4$ alkyl), —NHC(O)(phenyl), —N(C$_1$-C$_4$ alkyl)C(O)(C$_1$-C$_4$ alkyl), —N(C$_1$-C$_4$ alkyl)C(O) (phenyl), —C(O)C$_1$-C$_4$ alkyl, —C(O)C$_1$-C$_4$ phenyl, —C(O) C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

"Aryl" encompasses:
- 5- and 6-membered carbocyclic aromatic rings, for example, benzene;
- bicyclic ring systems wherein at least one ring is carbocyclic and aromatic, for example, naphthalene, indane, and tetralin; and
- tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses:
- 5- to 7-membered aromatic, monocyclic rings containing one or more, for example, from 1 to 4, or in certain embodiments, from 1 to 3, heteroatoms chosen from N, O, and S, with the remaining ring atoms being carbon; and
- bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered aromatic, monocyclic ring containing one or more, for example, from 1 to 4, or in certain embodiments, from 1 to 3, heteroatoms chosen from N, O, and S, with the remaining ring atoms being carbon, fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those S and O heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, systems (as numbered from the linkage position assigned priority 1), such as 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above. Substituted heteroaryl also includes ring systems substituted with one or more oxide (—O$^-$) substituents, such as pyridinyl N-oxides.

In the term "heteroarylalkyl," heteroaryl and alkyl are as defined herein, and the point of attachment is on the alkyl group. This term encompasses, but is not limited to, pyridylmethyl, thiophenylmethyl, and (pyrrolyl)1-ethyl.

By "heterocycloalkyl" is meant a saturated or unsaturated aliphatic ring containing at least 2 carbon atoms in addition to 1-3 heteroatoms independently selected from oxygen, sulfur, and nitrogen, as well as combinations comprising at least one of the foregoing heteroatoms, provided that the ring is not aromatic. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl and thiomorpholinyl groups are also contemplated, including 2-morpholinyl and 3-morpholinyl (numbered wherein the oxygen is assigned priority 1). Heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

As used herein, "modulation" refers to a change in kinase activity as a direct or indirect response to the presence of compounds of Formula 1, relative to the activity of the kinase in the absence of the compound. The change may be an increase in activity or a decrease in activity, and may be due to the direct interaction of the compound with the kinase, or due to the interaction of the compound with one or more other factors that in turn affect kinase activity. For example, the presence of the compound may, for example, increase or decrease kinase activity by directly binding to the kinase, by causing (directly or indirectly) another factor to increase or decrease the kinase activity, or by (directly or indirectly) increasing or decreasing the amount of kinase present in the cell or organism.

The term "sulfanyl" includes the groups: —S-(optionally substituted alkyl), —S-(optionally substituted aryl), —S-(optionally substituted heteroaryl), and —S-(optionally substituted heterocycloalkyl). Hence, sulfanyl includes the group C$_1$-C$_6$ alkylsulfanyl.

The term "sulfinyl" includes the groups: —S(O)—H, —S(O)-(optionally substituted alkyl), —S(O)-optionally substituted aryl), —S(O)-(optionally substituted heteroaryl), —S(O)-(optionally substituted heterocycloalkyl); and —S(O)-(optionally substituted amino).

The term "sulfonyl" includes the groups: —S($O_2$)—H, —S($O_2$)-(optionally substituted alkyl), —S($O_2$)-optionally substituted aryl), —S($O_2$)-optionally substituted heteroaryl), —S($O_2$)-(optionally substituted heterocycloalkyl), —S($O_2$)-(optionally substituted alkoxy), —S($O_2$)-optionally substituted aryloxy), —S($O_2$)-optionally substituted heteroaryloxy), —S($O_2$)-(optionally substituted heterocyclyloxy); and —S($O_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, further such as up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NRCCOR^b$, —$NR^cCO_2R^a$, —$NR^cCONR^bR^c$, —$CO_2R^b$, —$CONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, further such as up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, $SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "substituted alkoxy" refers to alkoxy wherein the alkyl constituent is substituted (i.e., —O-(substituted alkyl)) wherein "substituted alkyl" refers to alkyl wherein one or more (such as up to 5, further such as up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl). In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

The term "substituted alkoxycarbonyl" refers to the group (substituted alkyl)O—C(O)— wherein the group is attached to the parent structure through the carbonyl functionality and wherein substituted refers to alkyl wherein one or more (such as up to 5, further such as up to 3) hydrogen atoms are replaced by a substituent independently chosen from:

—$R^a$, —O$R^b$, —O($C_1$-$C_2$ alkyl)O— (e.g., methylenedioxy-), —S$R^b$, guanidine, guanidine wherein one or more of the guanidine hydrogens are replaced with a lower-alkyl group, —N$R^b R^c$, halo, cyano, nitro, —CO$R^b$, —CO$_2 R^b$, —CON$R^b R^c$, —OCO$R^b$, —OCO$_2 R^a$, —OCON$R^b R^c$, —N$R^c$CO$R^b$, —N$R^c$CO$_2 R^a$, —N$R^c$CON$R^b R^c$, —CO$_2 R^b$, —CON$R^b R^c$, —N$R^c$CO$R^b$, —SO$R^a$, —SO$_2 R^a$, —SO$_2$N$R^b R^c$, and —N$R^c$SO$_2 R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" refers to the group —NH$R^d$ or —N$R^d R^d$ where each $R^d$ is independently chosen from: optionally substituted alkyl, optionally substituted cycloalkyl, optionally substituted acyl, optionally substituted aminocarbonyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, further such as up to 3) hydrogen atoms are replaced by a substituent independently chosen from:

—$R^a$, —O$R^b$, —O($C_1$-$C_2$ alkyl)O— (e.g., methylenedioxy-), —S$R^b$, guanidine, guanidine wherein one or more of the guanidine hydrogens are replaced with a lower-alkyl group, —N$R^b R^c$, halo, cyano, nitro, —CO$R^b$, —CO$_2 R^b$, —CON$R^b R^c$, —OCO$R^b$, —OCO$_2 R^a$, —OCON$R^b R^c$, —N$R^c$CO$R^b$, —N$R^c$CO$_2 R^a$, —N$R^c$CON$R^b R^c$, —CO$_2 R^b$, —CON$R^b R^c$, —N$R^c$CO$R^b$, —SO$R^a$, —SO$_2 R^a$, —SO$_2$N$R^b R^c$, and —N$R^c$SO$_2 R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl); and wherein optionally substituted acyl, optionally substituted aminocarbonyl, alkoxycarbonyl, sulfinyl and sulfonyl are as defined herein.

The term "substituted amino" also refers to N-oxides of the groups —NH$R^d$ and —N$R^d R^d$, each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds of Formula 1 include, but are not limited to, optical isomers of compounds of Formula 1, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with carbon-carbon double bonds. Where compounds of Formula 1 exists in various tautomeric forms, chemical entities of the present invention include all tautomeric forms of the compound. Compounds of Formula 1 also include crystal forms including polymorphs and clathrates.

Chemical entities of the present invention include, but are not limited to compounds of Formula 1 and all pharmaceutically acceptable forms thereof. Pharmaceutically acceptable forms of the compounds recited herein include pharmaceutically acceptable salts, solvates, chelates, non-covalent complexes, and prodrugs thereof. In certain embodiments, the compounds described herein are in the form of pharmaceutically acceptable salts. Hence, the terms "chemical entity" and "chemical entities" also encompass pharmaceutically acceptable salts, solvates, chelates, non-covalent complexes, and prodrugs.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium.

In addition, if the compound of Formula 1 is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula 1. The term "prodrugs" includes any compounds that become compounds of Formula 1 when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula 1.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility. For example an active agent may be an anti-cancer therapeutic.

The term "therapeutically effective amount" of a chemical entity of this invention means an amount effective, when administered to a human or non-human patient, to treat a disease, e.g., a therapeutically effective amount may be an amount sufficient to treat a disease or disorder responsive to kinase inhibition. The therapeutically effective amount may be ascertained experimentally, for example by assaying blood concentration of the chemical entity, or theoretically, by calculating bioavailability.

By "significant" is meant any detectable change that is statistically significant in a standard parametric test of statistical significance such as Student's T-test, where $p<0.05$.

"Patient" refers to an animal, such as a mammal, for example a human, that has been or will be the object of treatment, observation or experiment. The methods of the invention can be useful in both human therapy and veterinary applications. In some embodiments, the patient is a mammal, and in some embodiments the patient is human. In some embodiments, the patient is chosen from cats and dogs.

By "angiogenic kinase" is meant a kinase involved in angiogenesis and includes but is not limited to a kinase chosen from $EphB_4$ VEGFR2 and PDGFRβ.

By "oncogenic kinase" is meant a kinase having a direct role in a cell signaling pathway that leads to cellular transformation. When overexpressed or aberrantly expressed, such kinases may have oncogenic activity. Oncogenic kinases include but are not limited to c-Kit.

"Treatment" or "treating" means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Diseases or disorders responsive to kinase modulation" refer to pathologic conditions that depend, at least in part, on the activity of one or more protein kinases, for example, angiogenic kinases and/or oncogenic kinases. Kinases either directly or indirectly participate in the signal transduction pathways of a variety of cellular activities including cell proliferation, differentiation, and invasion. Diseases responsive to kinase modulation include but are not limited to tumor growth, angiogenesis supporting solid tumor growth, and diseases characterized by excessive local vascularization such as diabetic retinopathy, macular degeneration, and inflammation.

"Change in angiogenesis" refers to a change in the vascular network or quality of vasculature. Change in angiogenesis may be measured by many parameters and, for instance, may be assessed by delayed appearance of neovascular structures, slowed development of neovascular structures, decreased occurrence of neovascular structures, changes in vascular permeability, changes in blood flow, slowed or decreased severity of angiogenesis-dependent disease effects, arrested angiogenic growth, or regression of previous angiogenic growth.

Provided herein is at least one chemical entity chosen from compounds of Formula 1

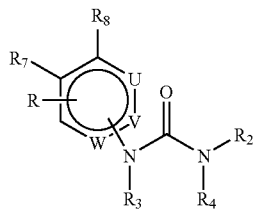

Formula 1 and pharmaceutically acceptable salts, solvates, chelates, non-covalent complexes, and prodrugs thereof, wherein U, V, and W are chosen from CH and N, provided that no more than two of U, V, and W are N;

R represents 0 to 2 substituents independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, sulfanyl, sulfinyl, sulfonyl, optionally substituted aryl, optionally substituted heteroaryl, and optionally substituted heterocycloalkyl;

$R_7$ and $R_8$, taken together with the carbons to which they are bound, form a fused 5- to 7-membered ring chosen from fused 5- to 7-membered cycloalkyl rings, fused 5- to 7-membered heteroaryl rings and fused 5- to 7-membered heterocyclic rings, wherein the fused 5- to 7-membered ring is substituted with a group —$(Z_1)_m R_1$ wherein $R_1$ is chosen from optionally substituted aryl and optionally substituted heteroaryl;

$Z_1$ is —$CR_5 R_6$— wherein each $R_5$ and $R_6$ is independently chosen from hydrogen, optionally substituted $C_1$-$C_6$ alkyl, and halo; and m is chosen from 0, 1, and 2;

$R_2$ is optionally substituted aryl; and $R_3$ and $R_4$ are each independently chosen from hydrogen, optionally substituted $C_1$-$C_6$ alkyl, optionally substituted aryl, and optionally substituted heteroaryl, provided that when $R_7$ and $R_8$, taken together with the carbons to which they are bound, form a fused 5- to 7-membered ring other than a fused 4,5-dihydro-1H-imidazole ring, then at least one of U, V, and W is nitrogen.

In certain embodiments, $R_7$ and $R_8$, taken together with the carbons to which they are bound, form a substituted fused ring chosen from substituted pyrazolyl, substituted imidazolyl, substituted isoxazolyl, substituted oxazolyl, substituted thiazolyl, substituted thiadiazolyl, substituted triazolyl, substituted 4,5-dihydro-1H-imidazolyl, and substituted pyrrolyl.

In certain embodiments, $R_7$ and $R_8$, taken together with the carbons to which they are bound, form a substituted fused heteroaryl ring chosen from substituted 4,5-dihydro-1H-imidazolyl, substituted 1H-pyrrolyl and substituted 1H-pyrazolyl.

In certain embodiments, $Z_1$ is —$CR_5 R_6$— and at least one of $R_5$ and $R_6$ is hydrogen. In certain embodiments, both of $R_5$ and $R_6$ are hydrogen.

In certain embodiments, m is 0. In certain embodiments, m is 1. In certain embodiments, m is 2.

In certain embodiments, m is 1 and at least one of $R_5$ and $R_6$ is hydrogen. In certain embodiments, m is 1 and both of $R_5$ and $R_6$ are hydrogen.

In certain embodiments, $R_1$ is optionally substituted heteroaryl.

In certain embodiments, $R_1$ is chosen from pyridinyl, substituted pyridinyl,

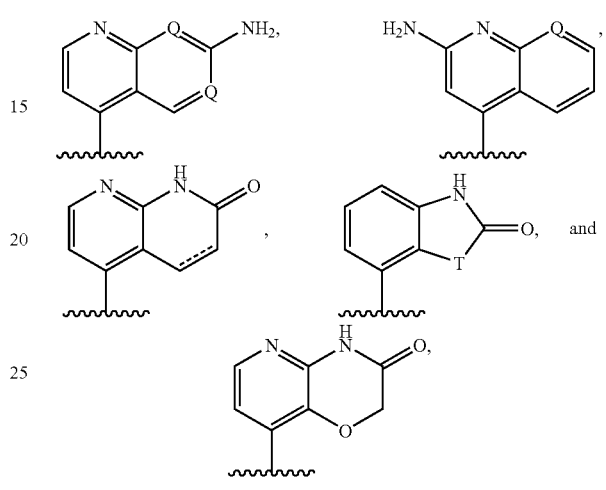

wherein Q is chosen from CH and N, T is chosen from CH, N, and O, and the wavy line represents the attachment point of $R_1$ to $Z_1$.

In certain embodiments, $R_1$ is chosen from pyridinyl and substituted pyridinyl wherein substituted pyridinyl is chosen from mono-, di-, and tri-substituted pyridinyls and wherein substituents are independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, sulfanyl, sulfinyl, sulfonyl, optionally substituted aryl, optionally substituted heteroaryl, and optionally substituted heterocycloalkyl.

In certain embodiments, $R_1$ is chosen from pyridinyl and substituted pyridinyl wherein substituted pyridinyl is chosen from mono-, di-, and tri-substituted pyridinyls and wherein substituents are independently chosen from hydroxy, nitro, cyano, optionally substituted amino, halo, carboxy, optionally substituted $C_1$-$C_6$ alkyl, optionally substituted $C_1$-$C_6$ alkoxy, $C_1$-$C_6$ alkylsulfanyl, $C_1$-$C_6$ acyl, $C_1$-$C_6$ alkoxycarbonyl, optionally substituted heteroaryl, and optionally substituted heterocycloalkyl.

In certain embodiments, $R_1$ is chosen from pyridinyl and substituted pyridinyl wherein substituted pyridinyl is chosen from mono-, di-, and tri-substituted pyridinyls and wherein substituents are independently chosen from hydroxy, cyano, halo, optionally substituted $C_1$-$C_2$ alkyl, and optionally substituted $C_1$-$C_2$ alkoxy.

In certain embodiments, $R_1$ is chosen from pyridin-4-yl and substituted pyridin-4-yl wherein substituted pyridin-4-yl is chosen from mono-, di-, and tri-substituted pyridin-4-yls and wherein substituents are independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, sulfanyl, sulfinyl, sulfonyl, optionally substituted aryl, optionally substituted heteroaryl, and optionally substituted heterocycloalkyl.

In certain embodiments, $R_1$ is chosen from pyridin-4-yl and substituted pyridin-4-yl wherein substituted pyridin-4-yl is chosen from mono-, di-, and tri-substituted pyridin-4-yls and wherein substituents are independently chosen from hydroxy, nitro, cyano, optionally substituted amino, halo, carboxy, optionally substituted $C_1$-$C_6$ alkyl, optionally substituted $C_1$-$C_6$ alkoxy, $C_1$-$C_6$ alkylsulfanyl, $C_1$-$C_6$ acyl, $C_1$-$C_6$ alkoxycarbonyl, optionally substituted heteroaryl, and optionally substituted heterocycloalkyl.

In certain embodiments, $R_1$ is chosen from pyridin-4-yl and substituted pyridin-4-yl wherein substituted pyridin-4-yl is chosen from mono-, di-, and tri-substituted pyridin-4-yls and wherein substituents are independently chosen from hydroxy, cyano, halo, optionally substituted $C_1$-$C_2$ alkyl, and optionally substituted $C_1$-$C_2$ alkoxy. In certain embodiments, $R_1$ is pyridin-4-yl.

In some embodiments, R represents 1 or 2 substituents independently chosen from halo, $C_1$-$C_2$ alkyl, and $C_1$-$C_2$ alkoxy. In some embodiments, R represents 1 or 2 substituents independently chosen from halo, methyl, and methoxy. In some embodiments R represents a substituent chosen from halo, methyl, and methoxy. In some embodiments, R is absent.

In certain embodiments, $R_2$ is chosen from phenyl, substituted phenyl,

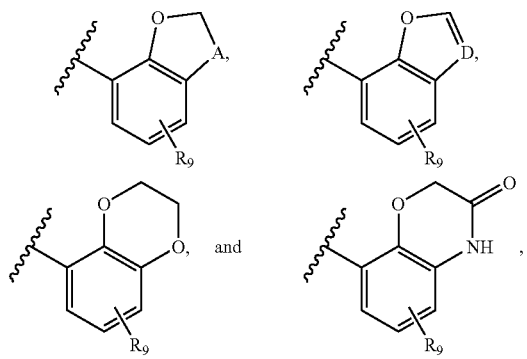

wherein
A is chosen from $CH_2$ and O,
D is chosen from CH and N,
the wavy line represents the attachment point of $R_2$ to the urea group of Formula 1, and
$R_9$ is chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, optionally substituted aryloxy, sulfanyl, sulfinyl, sulfonyl, optionally substituted aryl, optionally substituted heteroaryl, and optionally substituted heterocycloalkyl.

In certain embodiments, $R_2$ is chosen from phenyl and substituted phenyl wherein substituted phenyl is chosen from mono-, di-, and tri-substituted phenyls and wherein substituents are independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, optionally substituted aryloxy, sulfanyl, sulfinyl, sulfonyl, optionally substituted aryl, optionally substituted heteroaryl, and optionally substituted heterocycloalkyl.

In certain embodiments, $R_2$ is chosen from phenyl and substituted phenyl wherein substituted phenyl is chosen from mono-, di-, and tri-substituted phenyls and wherein substituents are independently chosen from hydroxy, nitro, cyano, optionally substituted amino, halo, carboxy, optionally substituted $C_1$-$C_6$ alkyl, optionally substituted $C_1$-$C_6$ alkoxy, optionally substituted phenoxy, $C_1$-$C_6$ alkylsulfanyl, $C_1$-$C_6$ acyl, $C_1$-$C_6$ alkoxycarbonyl, optionally substituted heteroaryl, and optionally substituted heterocycloalkyl.

In certain embodiments, $R_2$ is chosen from phenyl and substituted phenyl wherein substituted phenyl is chosen from mono-, di-, and tri-substituted phenyls and wherein substituents are independently chosen from hydroxy, cyano, halo, optionally substituted $C_1$-$C_2$ alkyl, phenoxy, and optionally substituted $C_1$-$C_2$ alkoxy.

In certain embodiments, $R_2$ is chosen from phenyl and substituted phenyl wherein substituted phenyl is chosen from mono-, di-, and tri-substituted phenyls and wherein substituents are independently chosen from halo, methyl, methoxy, ethoxy, and trifluoromethyl.

In certain embodiments, $R_3$ and $R_4$ are each independently chosen from hydrogen and methyl. In certain embodiments, $R_3$ and $R_4$ are hydrogen.

Also provided is at least one chemical entity chosen from compounds of Formula 2

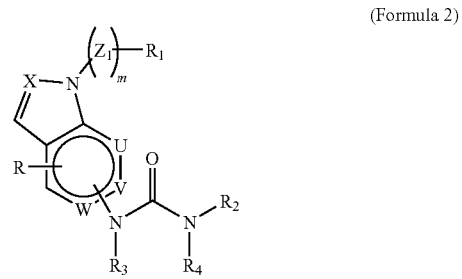
(Formula 2)

and pharmaceutically acceptable salts, solvates, chelates, non-covalent complexes, and prodrugs thereof, wherein U, V, W, R, $R_1$, $Z_1$, m, $R_2$, $R_3$ and $R_4$ are as described for compounds of Formula 1, and further wherein X is chosen from CH and N.

In certain embodiments, X is N. In certain embodiments, X is CH.

Also provided is at least one chemical entity chosen from compounds of Formula 3

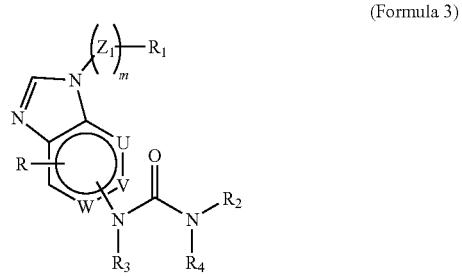
(Formula 3)

and pharmaceutically acceptable salts, solvates, chelates, non-covalent complexes, and prodrugs thereof, wherein
U, V, W, R, $R_1$, $Z_1$, m, $R_2$, $R_3$, and $R_4$ are as described for compounds of Formula 1.

Also provided is at least one chemical entity chosen from compounds of Formula 4

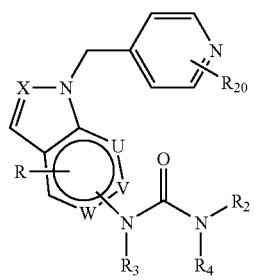

(Formula 4)

and pharmaceutically acceptable salts, solvates, chelates, non-covalent complexes, and prodrugs thereof, wherein X, U, V, W, R, $R_2$, $R_3$ and $R_4$ are as described for Formula 2, and further wherein $R_{20}$ represents 0 to 3 substituents independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, sulfanyl, sulfinyl, sulfonyl, optionally substituted aryl, optionally substituted heteroaryl, and optionally substituted heterocycloalkyl.

In certain embodiments, $R_{20}$ is absent.

Also provided is at least one chemical entity chosen from compounds of Formula 5

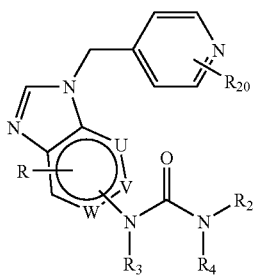

(Formula 5)

and pharmaceutically acceptable salts, solvates, chelates, non-covalent complexes, and prodrugs thereof, wherein U, V, W, R, $R_2$, $R_3$ and $R_4$ are as described for Formula 3, and further wherein.

$R_{20}$ represents 0 to 3 substituents independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, sulfanyl, sulfinyl, sulfonyl, optionally substituted aryl, optionally substituted heteroaryl, and optionally substituted heterocycloalkyl.

Also provided is at least one chemical entity chosen from compounds of Formula 6

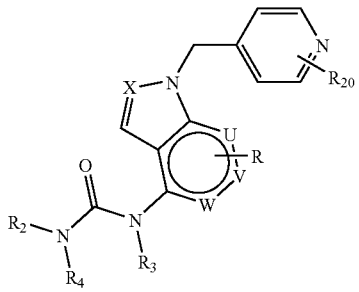

(Formula 6)

and pharmaceutically acceptable salts, solvates, chelates, non-covalent complexes, and prodrugs thereof, wherein X, U, V, W, R, $R_2$, $R_3$, $R_4$, and $R_{20}$ are as described for Formula 4.

Also provided is at least one chemical entity chosen from compounds of Formula 7

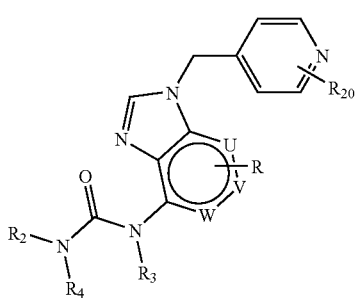

(Formula 7)

and pharmaceutically acceptable salts, solvates, chelates, non-covalent complexes, and prodrugs thereof, wherein U, V, W, R, $R_2$, $R_3$, $R_4$, and $R_{20}$ are as described for Formula 5.

Also provided is at least one chemical entity chosen from compounds of Formula 8

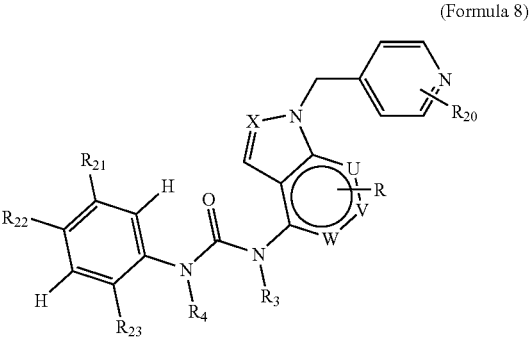

(Formula 8)

and pharmaceutically acceptable salts, solvates, chelates, non-covalent complexes, and prodrugs thereof, wherein X, U, V, W, R, $R_3$, $R_4$, and $R_{20}$ are as described for Formula 6 and further wherein $R_{21}$ is chosen from hydrogen, halo and optionally substituted lower alkyl;

$R_{22}$ is chosen from hydrogen, halo, lower alkoxy, and lower alkyl; and $R_{23}$ is chosen from hydrogen, lower alkyl, optionally substituted phenoxy, lower alkoxy, and halo Also provided is at least one chemical entity chosen from compounds of Formula 9

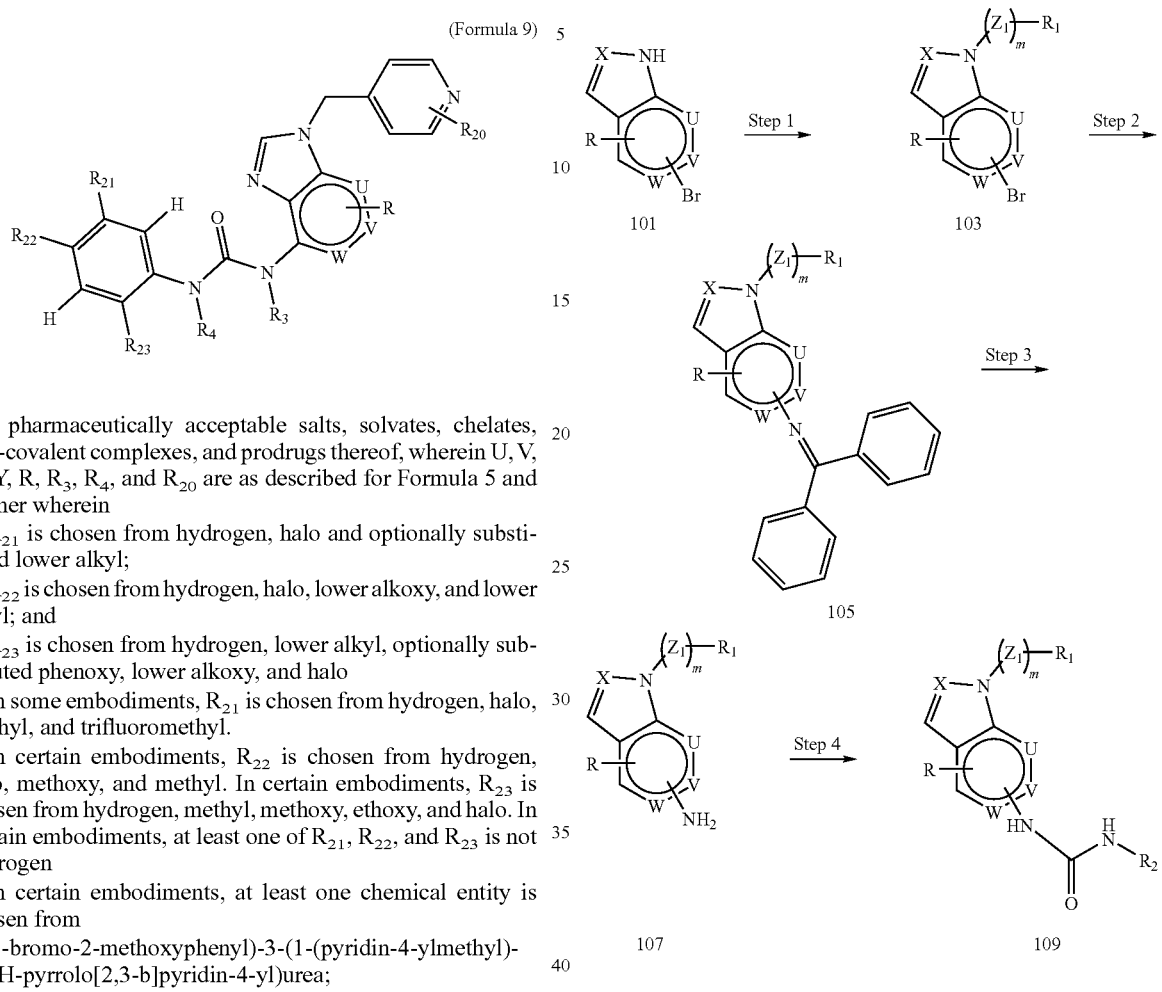

(Formula 9)

and pharmaceutically acceptable salts, solvates, chelates, non-covalent complexes, and prodrugs thereof, wherein U, V, W, Y, R, $R_3$, $R_4$, and $R_{20}$ are as described for Formula 5 and further wherein $R_{21}$ is chosen from hydrogen, halo and optionally substituted lower alkyl;

$R_{22}$ is chosen from hydrogen, halo, lower alkoxy, and lower alkyl; and $R_{23}$ is chosen from hydrogen, lower alkyl, optionally substituted phenoxy, lower alkoxy, and halo In some embodiments, $R_{21}$ is chosen from hydrogen, halo, methyl, and trifluoromethyl.

In certain embodiments, $R_{22}$ is chosen from hydrogen, halo, methoxy, and methyl. In certain embodiments, $R_{23}$ is chosen from hydrogen, methyl, methoxy, ethoxy, and halo. In certain embodiments, at least one of $R_{21}$, $R_{22}$, and $R_{23}$ is not hydrogen In certain embodiments, at least one chemical entity is chosen from 1-(5-bromo-2-methoxyphenyl)-3-(1-(pyridin-4-ylmethyl)-1H-pyrrolo[2,3-b]pyridin-4-yl)urea;

1-(5-chloro-2-methoxyphenyl)-3-(1-(pyridin-4-ylmethyl)-1H-pyrrolo[2,3-b]pyridin-4-yl)urea;

1-(5-Bromo-2-methoxy-phenyl)-3-(1-pyridin-4-ylmethyl-1H-benzoimidazol-4-yl)-urea;

1-(2-Methoxy-5-trifluoromethyl-phenyl)-3-(1-pyridin-4-ylmethyl-1H-benzoimidazol-4-yl)-urea;

1-(5-Bromo-2-methoxy-phenyl)-3-(1-quinolin-4-ylmethyl-1H-benzoimidazol-4-yl)-urea;

1-(5-Bromo-2-methoxy-phenyl)-3-(5-methyl-1-quinolin-4-ylmethyl-1H-benzoimidazol-4-yl)-urea;

1-(5-Bromo-2-methoxy-phenyl)-3-(5-methyl-1-pyridin-4-ylmethyl-1H-benzoimidazol-4-yl)-urea;

1-(2-Methoxy-5-trifluoromethyl-phenyl)-3-(5-methyl-1-pyridin-4-ylmethyl-1H-benzoimidazol-4-yl)-urea;

1-(4-Chloro-3-trifluoromethyl-phenyl)-3-(5-methyl-1-pyridin-4-ylmethyl-1H-benzoimidazol-4-yl)-urea; and 1-(5-Methyl-1-pyridin-4-ylmethyl-1H-benzoimidazol-4-yl)-3-(4-methyl-3-trifluoromethylphenyl)-urea; and pharmaceutically acceptable salts, solvates, chelates, non-covalent complexes, and prodrugs thereof.

Methods for obtaining the novel compounds described herein will be apparent to those of ordinary skill in the art, suitable procedures being described, for example, in the reaction scheme and example below, and in the references cited herein.

Referring to Reaction Scheme 1, Step 1, an excess (such as about 1.5 equivalents) of a compound of Formula 101 in an inert solvent such as DMF is cooled to about −15° C. An excess (such as about 2 equivalents) of a base, such as sodium hydride (for example, a 60% dispersion of sodium hydride in mineral oil) is then added and the reaction is stirred at about −15° C. for about 25 min. A compound of Formula $R_1$-$(Z_1)_m$-Q wherein Q is a leaving group, for example, halo, is added and the reaction mixture is stirred at about −15° C. for a further 5 min. After such time the cooling bath is removed and the reaction is stirred for about 30 min at ambient temperature. Additional compound of Formula $R_1$-$(Z_1)_m$-Q and base may be added and the reaction may be stirred at ambient temperature for an additional 30 minutes. The product, a compound of Formula 103, is isolated and optionally purified.

Referring to Reaction Scheme 1, Step 2, to a solution of about 0.3 equivalent of rac-2,2'-bis(diphenylphosphino)-1,1'-binapthyl, about 0.1 equivalent of $Pd_2dba_3$, and an excess (such as about 1.4 equivalents) of a base, such as sodium tert-butoxide is added a solution of a compound of Formula 103 in an inert solvent such as toluene followed by an excess (such as about 1.2 equivalents) of benzophenone imine. The reaction is heated at reflux for about 2 h. The product, a compound of Formula 105, is isolated and optionally purified.

Referring to Reaction Scheme 1, Step 3, a solution of a compound of Formula 105 in an inert solvent such as THF is treated with acid, such as aqueous hydrochloric acid, for example, 2N hydrochloric acid. The reaction is stirred at room temperature for about 1 h. The product, a compound of Formula 107, is isolated and optionally purified.

Referring to Reaction Scheme 1, Step 4, to a solution of a compound of Formula 107 in an inert solvent such as dichloromethane and/or dimethylformamide (for example, 3:1 dichloromethane:dimethylformamide) is added about one equivalent of an isocyanate of the formula $R_2$—NCO. The product, a compound of Formula 109, is isolated and optionally purified.

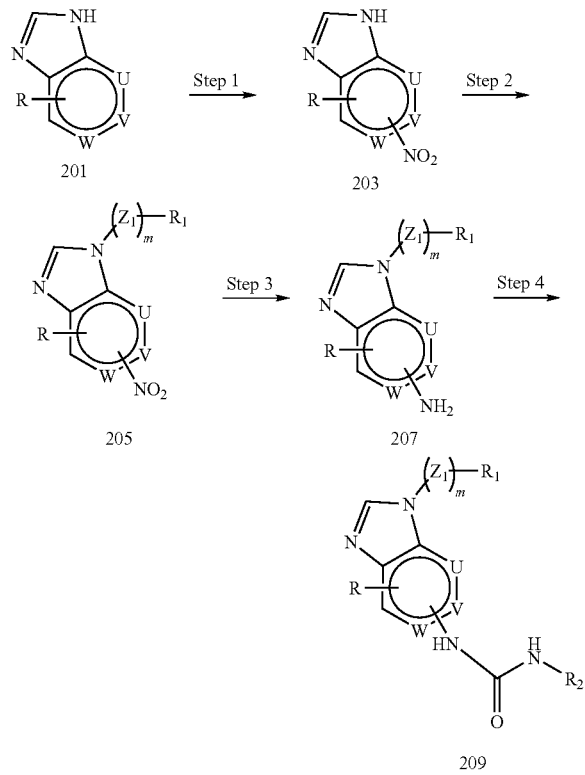

Referring to Reaction Scheme 2, Step 1, a solution of a compound of Formula 201 in 98% sulfuric acid is cooled to about 0° C. and treated portionwise with potassium nitrate over about 15 minutes. Once the last addition is complete, the reaction is stirred for 1 h at 0° C. The product, a compound of Formula 203, is isolated and optionally purified.

Referring to Reaction Scheme 2, Step 2, to a solution of about an equivalent of a compound of Formula $R_1$-$(Z_1)_m$-Q wherein Q is a leaving group such as chloro, in an inert solvent such as DMF is added about an equivalent of a base, such as sodium hydride (for example, a 60% dispersion of sodium hydride in mineral oil). The reaction mixture is stirred at room temperature. To the mixture is then added potassium carbonate and a compound of Formula 203. The product, a compound of Formula 205, is isolated and optionally purified.

Referring to Reaction Scheme 2, Step 3, a solution of a compound of Formula 205 and an excess (such as about 1.1 equivalents) of iron powder in acetic acid is stirred at about 50° C. for about 15 min. The product, a compound of Formula 207, is isolated and optionally purified.

Referring to Reaction Scheme 2, Step 4, to a solution of a compound of Formula 207 in an inert solvent such as $CH_2Cl_2$ is added about one equivalent of an isocyanate of the formula $R_2$—NCO. The product, a compound of Formula 209, is isolated and optionally purified.

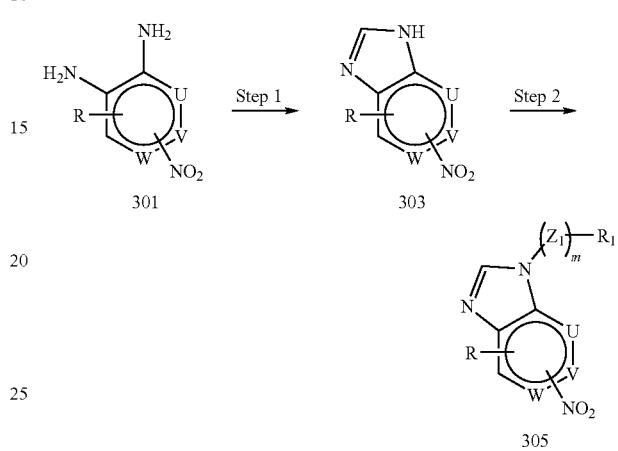

Referring to Reaction Scheme 3, Step 1, a solution of a compound of Formula 301, an excess (such as about 3 equivalents) of triethyl orthoformate, and p-toluenesulfonic acid in an inert solvent such as toluene is heated to reflux under nitrogen. The product, a compound of Formula 303, is isolated and optionally purified.

Referring to Reaction Scheme 3, Step 2, a solution of a compound of Formula 303, a base such as potassium carbonate, and a compound of Formula $R_1$-$(Z_1)_m$-Q wherein Q is a leaving group such as chloro, in an inert solvent such as DMF is stirred at room temperature. The product, a compound of Formula 305, is isolated and optionally purified.

In some embodiments, the chemical entities described herein are administered as a pharmaceutical composition or formulation. Accordingly, the invention provides pharmaceutical formulations comprising at least one chemical entity chosen from compounds of Formula 1 and pharmaceutically acceptable salts, solvates, chelates, non-covalent complexes, and prodrugs thereof, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the patient being treated. The vehicle can be inert or it can possess pharmaceutical benefits. The amount of vehicle employed in conjunction with the chemical entity is sufficient to provide a practical quantity of material for administration per unit dose of the chemical entity.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such as sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the chemical entity of the present invention.

A therapeutically effective amount of at least one chemical entity chosen from compounds of Formula 1 and pharmaceutically acceptable salts, solvates, chelates, non-covalent complexes, and prodrugs thereof, is mixed with a suitable pharmaceutical acceptable vehicle. In instances in which the chemical entity exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of the chemical entity described herein, the resulting mixture may be a solution, suspension, emulsion or the like. The form of the resulting mixture depends upon a number of factors, including the intended mode of administration and the solubility of the chemical entity in the chosen vehicle. The therapeutically effective amount of the chemical entity may be empirically determined.

Chemical entities described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral formulations contain from 0.1 to 99% of at least one chemical entity described herein. In some embodiments, oral formulations contain at least 5% (weight %) of at least one chemical entity described herein. Some embodiments contain from 25% to 50% or from 5% to 75% of at least one chemical entity described herein.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol, or sucrose. Such formulations may also contain a demulcent.

Chemical entities described herein can be incorporated into oral liquid preparations such as aqueous or oily suspensions, solutions, emulsions, syrups, or elixirs, for example. Moreover, formulations comprising these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are chosen form suspending agents, for example sodium carboxymethylcellulose, methylcellulose, hydropropylmethylcellulose, sodium alginate, polyvinylpyrrolidone, gum tragacanth and gum acacia; dispersing or wetting agents; naturally-occurring phosphatides, for example, lecithin, and condensation products of an alkylene oxide with fatty acids, for example polyoxyethylene stearate, and condensation products of ethylene oxide with long chain aliphatic alcohols, for example heptadecaethyleneoxycetanol, and condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the chemical entity is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Chemical entities described herein may be administered parenterally in a sterile medium. Parenteral administration includes subcutaneous injections, intravenous, intramuscular, intrathecal injection or infusion techniques. Chemical entities described herein, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Chemical entites described herein may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Chemical entities described herein may be formulated for local or topical application, such as for topical application to the skin and mucous membranes, such as in the eye, in the form of gels, creams, and lotions and for application to the eye. Topical compositions may be in any form including, for example, solutions, creams, ointments, gels, lotions, milks, cleansers, moisturizers, sprays, skin patches, and the like.

Such solutions may be formulated as 0.01%-10% isotonic solutions, pH from 2 to 12, such as from 5 to 7, with appropriate salts. Chemical entities described herein may also be formulated for transdermal administration as a transdermal patch.

Topical compositions comprising at least one chemical entity described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Chemical entities described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine, and phosphatidylcholines.

Other compositions useful for attaining systemic delivery of the chemical entity include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

The compositions of the present invention may also optionally comprise an activity enhancer. The activity enhancer can be chosen from a wide variety of molecules that function in different ways to enhance or be independent of therapeutic effects of the chemical entities described herein. Particular classes of activity enhancers include skin penetration enhancers and absorption enhancers.

Pharmaceutical compositions of the invention may also contain additional active agents that can be chosen from a wide variety of molecules, which can function in different ways to enhance the therapeutic effects of at least one chemical entity described herein. These optional other active agents, when present, are typically employed in the compositions of the invention at a level ranging from 0.01% to 15%. Some embodiments contain from 0.1% to 10% by weight of the composition. Other embodiments contain from 0.5% to 5% by weight of the composition.

The invention can include packaged pharmaceutical formulations. Such packaged formulations include a pharmaceutical composition comprising at least one chemical entity chosen from compounds of Formula 1 and pharmaceutically acceptable salts, solvates, chelates, non-covalent complexes, and prodrugs, in a container and instructions for using the composition to treat a mammal (typically a human patient). In some embodiments, the instructions are for using the pharmaceutical composition to treat a patient suffering from a disease responsive to kinase inhibition. The invention includes providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the chemical entities can be administered alone, as mixtures, or in combination with other active agents.

The compounds of the present invention can be useful for the treatment of diseases and disorders responsive to kinase modulation. As used herein, "modulation" refers to a change in kinase activity as a direct or indirect response to the presence of at least one chemical entity described herein, relative to the activity of the kinase in the absence of the chemical entity. The change may be an increase in activity or a decrease in activity, and may be due to the direct interaction of the chemical entity with the kinase, or due to the interaction of the chemical entity with one or more other factors that in turn affect kinase activity. For example, the presence of the chemical entity may increase or decrease kinase activity by directly binding to the kinase, by causing (directly or indirectly) another factor to increase or decrease the kinase activity, or by (directly or indirectly) increasing or decreasing the amount of kinase present in the cell or organism.

In certain embodiments, compounds described herein are modulators of protein kinases. In certain embodiments, the compounds described herein are inhibitors of the protein kinases. In certain embodiments, the compounds inhibit at least one kinase chosen from $EphB_4$, c-Kit, PDGFRβ, and VEGFR2 kinases. In certain embodiments, the compounds inhibit more than one kinase chosen from $EphB_4$, c-Kit, PDGFRβ, and VEGFR2 kinases.

Accordingly, the invention includes a method of treating a patient, such as a human patient, having a disease or disorder responsive to kinase modulation, comprising administering to the patient a therapeutically effective amount of at least one chemical entity described herein.

A method of treating a patient having a disease or disorder responsive to kinase modulation, particularly VEGFR2 modulation, comprising administering to the patient a therapeutically effective amount of one or more of the compounds of Formula I is provided.

Also provided is the use of at least one chemical entity described herein for the manufacture of a medicament for the treatment of a patient having a disease or disorder responsive to kinase modulation, particularly VEGFR2 modulation. Also provided is the use of at least one chemical entity described herein for the manufacture of a medicament for the treatment of a patient having angiogenesis.

In some embodiments, the chemical entities described herein inhibit at least one kinase chosen from $EphB_4$, c-Kit, PDGFRβ, and VEGFR2 and can be useful for the treatment of diseases and disorders responsive to modulation of at least one of such kinases. In some embodiments, the disease or disorder is characterized by angiogenesis supporting solid tumor growth or dysregulated local vascularization.

Methods of treatment also include modulating kinase activity, by inhibiting ATP binding or hydrolysis by a kinase or by some other mechanism, in vivo, in a patient suffering from a disease or disorder responsive to kinase modulation, by administering a therapeutically effective amount of at least one chemical entity described herein to inhibit kinase activity in vitro.

In some embodiments, the condition responsive to kinase modulation is cancer or a disease or disorder characterized by a change in angiogenesis.

The invention includes a method of treating a patient having cancer or a disease or disorder characterized by a change in angiogenesis by administering at least one chemical entity described herein. The invention provides methods of treatment in which a compound of the invention is the only active agent given to a patient and also includes methods of treatment in which at least one chemical entity described herein is given to a patient in combination with one or more additional active agents.

Certain compounds described herein can be useful for treating a patient suffering from a disease or disorder responsive to kinase modulation.

In certain embodiments, the conditions, diseases and/or disorders that are affected using compounds of Formula I and compositions comprising such compounds include, but are not limited to, psoriasis, angiogenesis, cancer (for example, chronic myelogenous leukemia, gastrointestinal stromal tumors, non-small cell lung cancer, breast cancer, ovarian cancer, recurrent ovarian cancer, prostate cancer such as hormonal refractory prostate cancer, kidney cancer, head and neck cancer, or colorectal cancer), immunoregulation (graft rejection), atherosclerosis, rheumatoid arthritis, Parkinson's disease, Alzheimer's disease, diabetes (for example insulin resistance or diabetic retinopathy), septic shock, and the like.

Because kinases play an active role in angiogenesis certain compounds described herein can be useful for modulating angiogenesis. Angiogenesis, the formation of new blood vessels from preexisting ones, plays a critical role in many pathological settings, including cancer, chronic inflammation, diabetic retinopathy and macular degeneration. Angiogenesis is regulated by multiple cell-signaling pathways, including pathways controlled by cellular kinases. Blocking angiogenesis, through the modulation of cell kinases, therefore, can represent effective approach to the treatment of diseases such as cancer. Thus methods of treatment include administering a therapeutically effective amount of at least one chemical entity described herein to treat these diseases or disorders, e.g., to decrease the symptoms or slow the progression of these diseases or disorders by inhibiting the rate of angiogenesis in a tissue.

The invention further includes methods for combination drug therapy, in which a compound of the invention is given to a patient together with one or more other active agents.

Thus in one embodiment the invention provides a method of treating cancer, which comprises administering to a patient in need thereof an effective amount of at least one chemical entity described herein together with a second active agent, which can be useful for treating cancer. For example the second agent may be an antitumor agent. Treatment with the second active agent may be prior to, concomitant with, or following treatment with at least one chemical entity described herein.

In certain embodiments, at least one chemical entity chosen from compounds of Formula 1, and pharmaceutically acceptable salts, solvates, chelates, non-covalent complexes, and prodrugs thereof, is combined with at least one second active agent in a single dosage form. Radiotherapeutic anti-tumor agents may also be used alone or in combination with chemotherapeutic agents. Suitable anti-tumor therapeutics that may be used in combination with at least one chemical entity described herein. Examples of anti-tumor therapeutics include, in general, microtubule-stabilizing agents (such as paclitaxel (also known as Taxol), docetaxel (also known as Taxotere), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Exemplary classes of anti-tumor therapeutics include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloro-methotrexate, mitomycin C, porfiromycin, herceptin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

In certain embodiments, at least one chemical entity chosen from compounds of Formula 1, and pharmaceutically acceptable salts, solvates, chelates, non-covalent complexes, and prodrugs thereof, can be administered in combination with an anti-inflammatory agent. Anti-inflammatory agents include NSAIDs, non-specific and COX-2 specific cyclooxgenase enzyme inhibitors, gold-containing compounds, corticosteroids, methotrexate, tumor necrosis factor receptor (TNF) receptors antagonists, immunosuppressants and methotrexate. Examples of NSAIDs include ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib. In certain embodiments, the anti-inflammatory agent can be a salicylate. Salicylates include acetylsalicylic acid or aspirin, sodium salicylate, and choline and magnesium salicylates.

The anti-inflammatory agent can also be a corticosteroid. For example, the corticosteroid may be cortisone, dexamethasone, methylprednisolone, prednisolone, prednisolone sodium phosphate, and prednisone. In certain embodiments, the anti-inflammatory agent can be a gold-containing compound such as gold, sodium thiomalate or auranofin. In certain embodiments, the anti-inflammatory agent can be a metabolic inhibitor such as a dihydrofolate reductase inhibitor, such as methotrexate or a dihydroorotate dehydrogenase inhibitor, such as leflunomide. Certain embodiments of the present disclosure include combinations in which at least one anti-inflammatory compound can be an anti-C5 monoclonal antibody (such as eculizumab or pexelizumab), a TNF antagonist, such as entanercept, or infliximab, which is an anti-TNF alpha monoclonal antibody, and combinations in which at least one active agent is an immunosuppressant compound such as methotrexate, leflunomide, cyclosporine, tacrolimus, azathioprine, or mycophenolate mofetil.

Dosage levels of the order of from 0.1 mg to 140 mg per kilogram, such as 1 to 50 mg per kilogram, of body weight per day can be useful in the treatment of the above-indicated conditions (0.5 mg to 7 g per patient per day). The amount of active ingredient that may be combined with the carrier materials to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In certain embodiments, a dosage regimen of 4 times daily or less is used. In certain embodiments, a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

EXAMPLES

The invention is further illustrated by the following non-limiting examples.

In the examples below, the following abbreviations have the following meanings. If an abbreviation is not defined, it has its generally accepted meaning.

| | |
|---|---|
| DME = | dimethyl ether |
| DMEM = | Dulbecco's modified Eagle's medium |
| DMF = | N,N-dimethylformamide |
| DMSO = | dimethylsulfoxide |
| g = | gram |
| h = | hour |
| mg = | milligram |
| min = | minutes |
| mL = | milliliter |
| mmol = | millimoles |
| mM = | millimolar |
| ng = | nanogram |
| nm = | nanometer |
| nM = | nanomolar |
| PBS = | phosphate buffered saline |
| µL = | microliter |
| µM = | micromolar |

Example 1

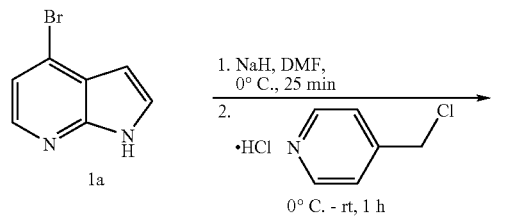

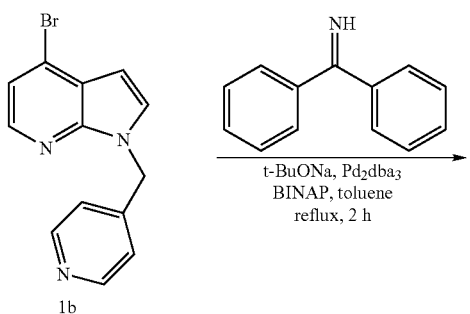

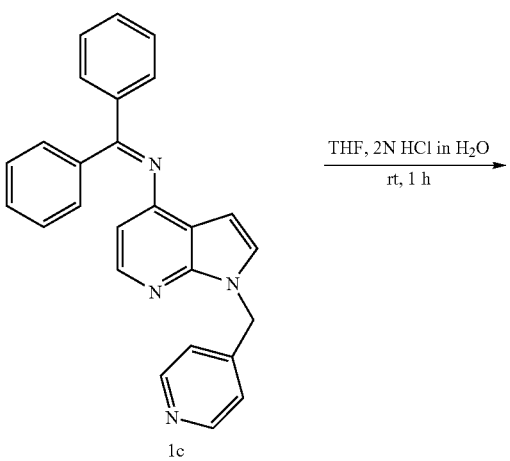

Compound 1a was prepared using the procedure described in *Org. Lett.* 2003, 5, 5023.

4-Bromo-1-pyridin-4-ylmethyl-1H-pyrrolo[2,3-b]pyridine (1b)

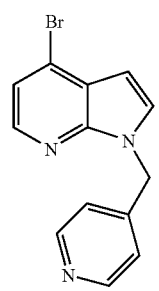

A 250-mL argon-purged round-bottomed flask equipped with a magnetic stirrer is charged with 4-Bromo-1H-pyrrolo [2,3-b]pyridine (0.70 g, 3.55 mmol) and DMF (25 mL) and the solution is cooled to −15° C. A 60% dispersion of sodium hydride in mineral oil (183 mg, 4.58 mmol) is then added and the reaction stirred at −15° C. for 25 min. The reaction is then charged with 4-picolylchloride hydrochloride (376 mg, 2.29 mmol) and stirred at −15° C. for a further 5 min. After such time the cooling bath is removed and the reaction is stirred for 30 min at ambient temperature. Additional 4-picolylchloride hydrochloride (117 mg, 0.71 mmol) and a 60% dispersion of sodium hydride in mineral oil (28 mg, 0.71 mmol) are then added and the reaction is stirred at ambient temperature for a further 30 min. The reaction is then poured into ethyl acetate (100 mL) and the mixture is washed with 3% aqueous sodium bicarbonate (1×100 mL), water (2×100 mL) and brine (1×100 mL). The organic layer is separated, dried over sodium sulfate and concentrated in vacuo to provide a residue, which is then purified by flash chromatography to afford 1b as a yellow solid.

N-(dipheylmethylene)-1-(pyridin-4-ylmethyl)-1H-pyrrolo[2,3-b]pyridin-4-amine (1c)

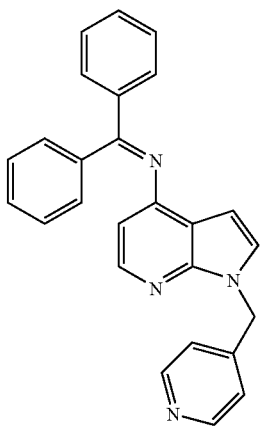

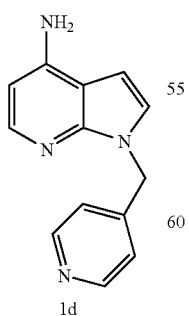

A 25-mL round-bottomed flask equipped with magnetic stirrer and reflux condenser is charged with rac-2,2'-bis (diphenylphosphino)-1,1'-binapthyl (0.040 g, 0.063 mmol), Pd₂dba₃ (0.019 g, 0.021 mmol) and sodium tert-butoxide (0.282 g, 2.94 mmol). The reaction vessel is then purged with a stream of nitrogen for 0.5 h. After such time, a solution of Compound 1b (0.600 g, 2.10 mmol) in toluene (6 mL) followed by benzophenone imine (0.45 g, 2.51 mmol) is added. The reaction is then heated at reflux for 2 h. After such time the reaction is cooled to room temperature and concentrated under reduced pressure. The resulting oil is then purified by column chromatography to afford Compound 1c as a yellow oil.

1-(Pyridin-4-yl)methyl-1H-pyrrolo[2,3-b]pyridin-4-ylamine (1d)

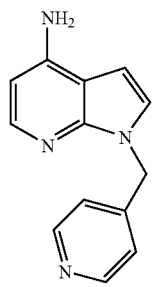
1d

A 25-mL round-bottomed flask equipped with magnetic stirrer is charged with Compound 1c (0.580 g, 1.49 mmol), THF (10 mL) and 2N hydrochloric acid (2.0 mL). The reaction is then stirred at room temperature for 1 h. After such time, the reaction is partitioned between ethyl acetate (15 mL) and water (15 mL). The aqueous layer is separated and washed with ethyl acetate (2×25 mL). After basifying to pH 9 with solid potassium carbonate in order to liberate the free base of Compound 1d, the aqueous layer is extracted with ethyl acetate (2×25 mL). The extracts are then combined and dried over sodium sulfate. The sodium sulfate is removed by filtration and the filtrate concentrated under reduced pressure. The resulting residue is then purified by column chromatography to afford Compound 1d as a white solid.

1-(5-Bromo-2-methoxy-phenyl)-3-(1-pyridin-4-ylmethyl-1H-pyrrolo[2,3-b]pyridin-4-yl)-urea (1e)

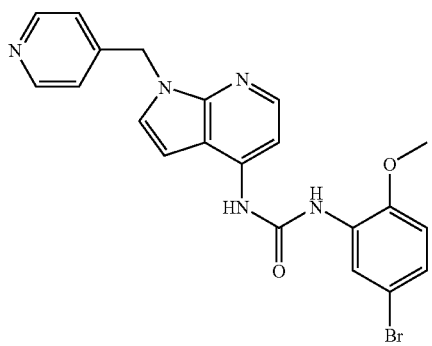
1e

To a solution of Compound 1d (50 mg, 0.2 mmol) in dichloromethane:dimethylformamide (4.0 mL, 3:1) is added 4-bromo-2-isocyanato-1-methoxy-benzene (50 mg, 0.2 mmol, 1 equiv.) and the reaction mixture is heated for 16 hrs, the solvent is then removed and the residue is purified using flash chromatography to afford Compound 1e as a white solid.

1-(5-Chloro-2-methoxy-phenyl)-3-(1-pyridin-4-ylmethyl-1H-pyrrolo[2,3-b]pyridin-4-yl)-urea (1f)

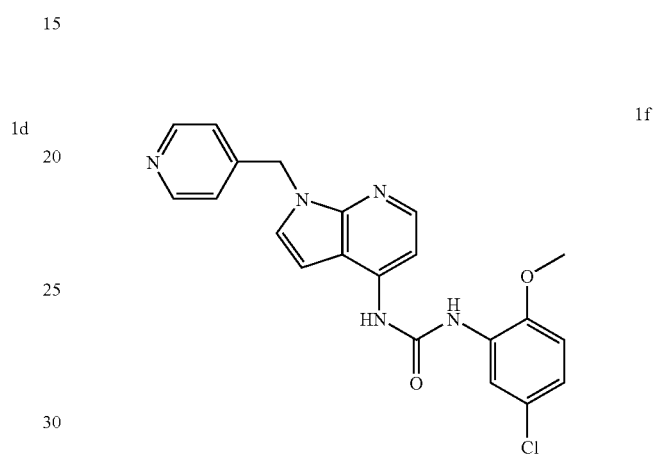
1f

Compound 1d (52 mg, 0.233 mmol) is dissolved in dichloromethane (5.0 mL) and 4-bromo-2-isocyanato-1-methoxy-benzene (1.0 equiv., 44 mg, 0.233 mmol) is then added and stirred at room temperature for 3 hours under nitrogen atmosphere. All solvent is then removed by rotary evaporation and the crude product is purified via preparative TLC to afford Compound 1f as an off-white solid.

Example 2

The following compounds were prepared using procedures similar to those described above. Those of ordinary skill in the art of organic synthesis will recognize when starting materials or reaction conditions should be varied to obtain the desired compound.

MS data reported in this example was obtained as follows:

MS conditions: Electrospray MS is performed on a MICROMASS LCT equipped with a LockSpray source for accurate mass measurements. Spectra are acquired in positive ion mode from 100-1000 Da at an acquisition rate of 1 spectrum/ 0.9 s with a 0.1 s interscan delay. The instrument is tuned for a resolution of 5000 (FWHM). Every 5$^{th}$ scan is taken from the reference position of the Lockspray source. Leucine enkephalin (556.2771 [M+H]⁺) is used as the reference, or lock mass.

| Structure | Name/MW | MS m/z (M + H) |
|---|---|---|
| | 1-(5-bromo-2-methoxyphenyl)-3-(1-(pyridin-4-ylmethyl)-1H-pyrrolo[2,3-b]pyridin-4-yl)urea<br>$C_{21}H_{18}BrN_5O_2$<br>451.06 | 452.24 |
| | 1-(5-chloro-2-methoxyphenyl)-3-(1-(pyridin-4-ylmethyl)-1H-pyrrolo[2,3-b]pyridin-4-yl)urea<br>$C_{21}H_{18}ClN_5O_2$<br>407.11 | 408.22 |
Example 3
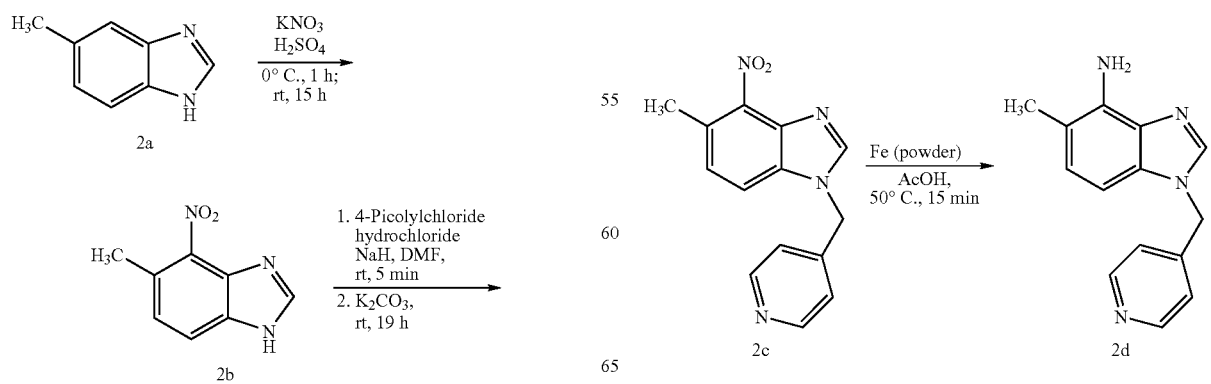

5-Methyl-4-nitro-1H-benzoimidazole (2b)

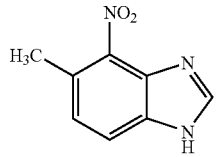

A 500-mL single-neck round-bottomed flask equipped with a magnetic stirrer was charged with compound 2a (7.45 g, 56.4 mmol) and 98% sulfuric acid (50 mL). The mixture was then cooled to 0° C. and treated portionwise with potassium nitrate (5.72 g, 56.5 mmol) over 15 minutes. Once the last addition was complete, the reaction was stirred for 1 h at 0° C. The ice bath was then removed and stirring continued at ambient temperature for 14 h. After this time the reaction was cooled to 0° C. and basified to pH 10 by the slow addition of 29% ammonium hydroxide (300 mL). The resulting suspension was filtered and the precipitate washed with water (3×100 mL). The filtrate was then extracted with ethyl acetate (3×100 mL) and the combined organic layers dried over sodium sulfate, filtered and concentrated under reduced pressure. The resulting residue and the above precipitate were combined and dried under reduced pressure at 50° C. Purification of this material by flash chromatography afforded compound 2b as a light yellow solid.

5-Methyl-4-nitro-1-(pyridin-4-yl)methyl-1H-benzimidazole (2c)

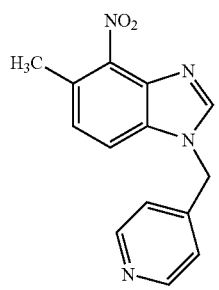

A 200-mL round-bottomed flask equipped with a magnetic stirrer was charged with 4-picolylchloride hydrochloride (1.20 g, 7.34 mmol) and DMF (30 mL) under argon. A 60% dispersion of sodium hydride in mineral oil (294 mg, 7.34 mmol) was added to the resulting solution and the reaction stirred at room temperature for 5 min. The reaction was then charged with potassium carbonate (3.55 g, 25.7 mmol), stirred at room temperature for 5 min and compound 2b (1.30 g, 7.34 mmol) was added. Once this addition was complete, the reaction was stirred at room temperature for 19 h. After this time the reaction was poured into ethyl acetate (1 L) and the resulting mixture washed with water (3×750 mL) followed by brine (750 mL). The resulting organic layer was dried over sodium sulfate, then filtered and the filtrate concentrated under reduced pressure providing a residue, which was purified by flash chromatography to afford compound 2c as a light-yellow solid.

5-Methyl-1-(pyridin-4-yl)methyl-1H-benzimidazol-4-ylamine (2d)

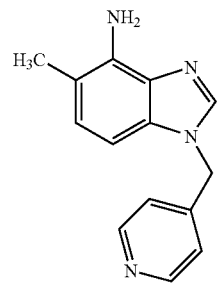

A 200-mL round-bottomed flask equipped with mechanical stirrer was charged with 5-Methyl-4-nitro-1-(pyridin-4-yl)methyl-1H-benzimidazole (881 mg, 3.46 mmol), iron powder (–325 mesh, 3.87 g, 6.92 mmol) and acetic acid (50 mL), and the resulting mixture stirred at 50° C. for 15 min. After this time the reaction was cooled to room temperature, diluted with 1:1 methylene chloride/methanol (1 L) and filtered through a pad of Celite 521. After washing the filter cake with 1:1 methylene chloride/methanol (2×50 mL), the filtrate was concentrated in vacuo. The resulting residue was dissolved in methylene chloride (50 mL) and vigorously stirred with 1M aqueous sodium hydroxide (50 mL). The resulting emulsion was filtered through a pad of Celite 521, the pad washed with methylene chloride (2×25 mL) and the organic layer of the filtrate separated and dried over sodium sulfate. Removal of the drying agent by filtration, followed by evaporation of the filtrate in vacuo gave a residue which was purified by flash chromatography. This purified material was dissolved in warm methylene chloride (15 mL) and the solution diluted with hexanes (35 mL). The resulting precipitate was filtered, washed with hexanes (3×100 mL) and dried under reduced pressure for 1.5 h to afford compound 2d as an off-white solid.

1-(5-Bromo-2-methoxy-phenyl)-3-(5-methyl-1-pyridin-4-ylmethyl-1H-benzoimidazol-4-yl)-urea (2e)

Compound 2d (100 mg, 0.42 mmol) is weighed into a round bottom flask and dissolved in dichloromethane (3 mL). 2-Isocyanato-1-methoxy-4-trifluoromethyl-benzene (90 mg, 0.42 mmol) is added as a solid and the homogeneous mixture is stirred for 4 h. The precipitate is collected via filtration and the solids are washed with ether and collected to yield compound 2e as a white amorphous solid.

1-(2-Methoxy-5-trifluoromethyl-phenyl)-3-(5-methyl-1-pyridin-4-ylmethyl-1H-benzoimidazol-4-yl)-urea (2f)

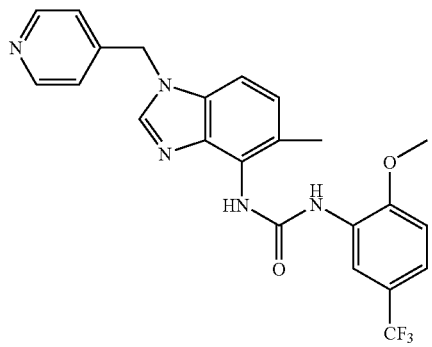

Compound 2d (100 mg, 0.42 mmol) is weighed into a round bottom flask and dissolved in dichloromethane (3 mL). 4-Bromo-2-isocyanato-1-methoxy-benzene (96 mg, 0.42 mmol) is added as a solid and the homogeneous mixture is stirred for 4 h. The precipitate is collected via filtration and are washed with ether and collected to yield the title compound as a white amorphous solid.

1-(4-Chloro-3-trifluoromethyl-phenyl)-3-(5-methyl-1-pyridin-4-ylmethyl-1H-benzoimidazol-4-yl)-urea (2g)

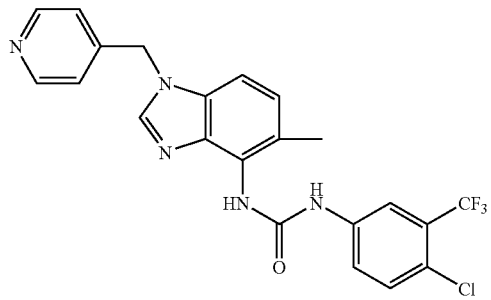

Compound 2d (100 mg, 0.42 mmol) is weighed into a round bottom flask and dissolved in dichloromethane (3 mL). 1-Chloro-4-isocyanato-2-trifluoromethyl-benzene (93 mg, 0.42 mmol) is added as a solid and the homogeneous mixture is stirred for 4 h. The precipitate is collected via filtration and are washed with ether and collected to yield compound 2g as a white amorphous solid.

1-(5-Methyl-1-pyridin-4-ylmethyl-1H-benzoimidazol-4-yl)-3-(4-methyl-3-trifluoromethyl-phenyl)-urea (2h)

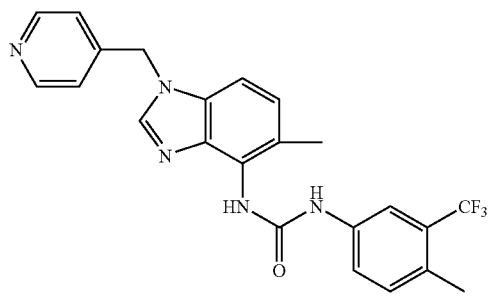

Compound 2d (100 mg, 0.42 mmol) is weighed into a round bottom flask and dissolved in dichloromethane (3 mL). 4-Isocyanato-1-methyl-2-trifluoromethyl-benzene (85 mg, 0.42 mmol) is added as a solid and the homogeneous mixture is stirred for 4 h. The precipitate is collected via filtration and the solids are washed with ether and collected to yield compound 2h as a white amorphous solid.

Example 4

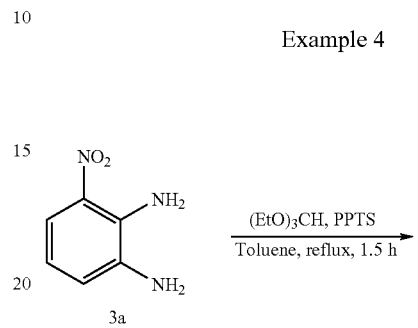

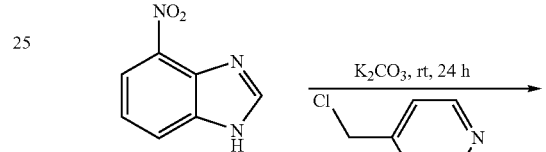

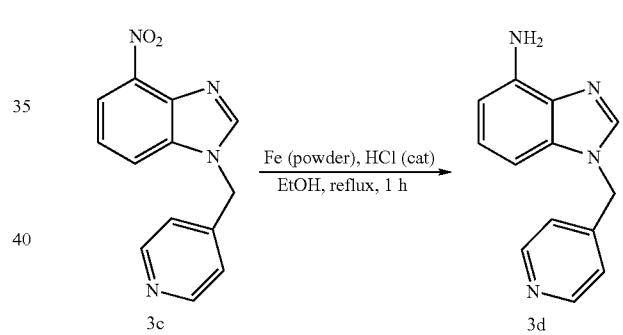

4-Nitro-1H-benzimidazole (3b)

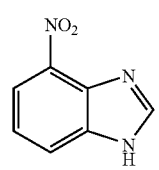

A 500-mL round-bottomed flask equipped with a magnetic stirrer and reflux condenser was charged with compound 3a (4.70 g, 30.6 mmol), toluene (200 mL), triethyl orthoformate (13.6 g, 92.0 mmol) and p-toluenesulfonic acid (386 mg, 1.5 mmol) and the mixture then heated to reflux under nitrogen. After 1.5 h the reaction was cooled to 0° C. and the resulting precipitate filtered, washed with ether (3×50 mL) and dried in the vacuum oven to afford compound 3b as a tan powder.

4-Nitro-1-(pyridin-4-yl)methyl-1H-benzimidazole (3c)

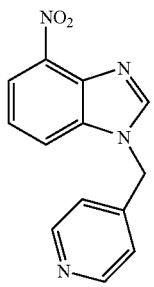

3c

A 500-mL round-bottomed flask equipped with a magnetic stirrer and nitrogen inlet is charged with compound 3b (3.30 g, 30.6 mmol), potassium carbonate (8.95 g, 64.8 mmol), anhydrous DMF (200 mL) and 4-chloromethylpyridine hydrochloride (3.98 g, 24.3 mmol) and the mixture is then stirred under nitrogen for 24 h at ambient temperature. After such time the reaction is partitioned between water (200 mL) and ethyl acetate (200 mL). The aqueous layer is separated and extracted with ethyl acetate (6×250 mL). The combined organic extracts are dried with sodium sulfate, and the drying agent is filtered off. The filtrate is then concentrated under vacuum to give a brown solid, which is purified by column chromatography to afford compound 3c as a yellow solid.

1-(Pyridin-4-yl)methyl-1H-benzimidazol-4-ylamine (3d)

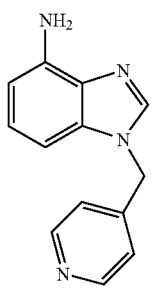

3d

Using the same general procedure as described above for the preparation of 5-methyl-1-(pyridin-4-yl)methyl-1H-benzimidazol-4-ylamine (2d), reduction of 4-nitro-(1-pyridin-4-yl)methyl-1H-benzimidazole 3c (1.71 g) gave 3d as a pale yellow powder.

1-(5-Bromo-2-methoxy-phenyl)-3-(1-pyridin-4-ylmethyl-1H-benzoimidazol-4-yl)-urea

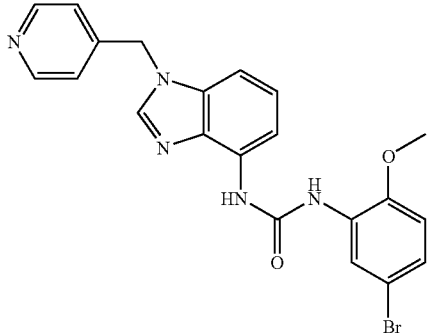

2i

Compound 3d (75 mg, 0.334 mmol) is dissolved in dimethylformamide/dichloromethane (1:4, 5.0 mL) and 4-bromo-2-isocyanato-1-methoxy-benzene (1.0 equiv., 76 mg, 0.334 mmol) is added at room temperature and allowed to react for 16 hours under nitrogen atmosphere. All solvent is then removed on a rotary evaporator and toluene (3×25 mL) is added and stripped off to remove residual dimethylformamide. The crude solid is then triturated using ethyl ether, and the resulting solid is then filtered and dried yielding compound 2i as a white solid.

1-(2-Methoxy-5-trifluoromethyl-phenyl)-3-(1-pyridin-4-ylmethyl-1H-benzoimidazol-4-yl)-urea (2j)

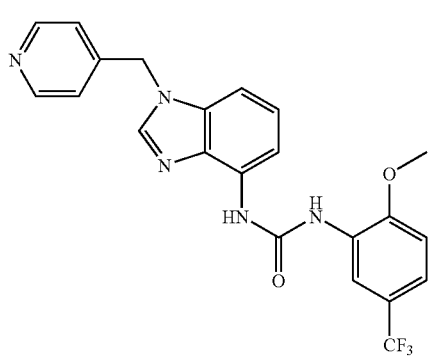

2j

Compound 3d (75 mg, 0.334 mmol) is dissolved in dimethylformamide/dichloromethane (1:4, 5.0 mL) and 2-isocyanato-1-methoxy-4-trifluoromethyl-benzene (1.0 equiv., 73 mg, 0.334 mmol) is added at room temperature and allowed to react for 16 hours under nitrogen atmosphere. All solvent is then removed on a rotary evaporator and toluene (3×25 mL) is added and stripped off to remove residual dimethylformamide. The crude solid is then triturated using ethyl ether, and the resulting solid is then filtered and dried yielding title compound as a white solid.

Example 5

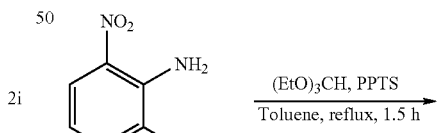

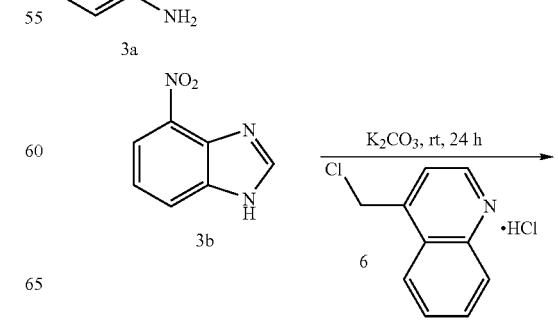

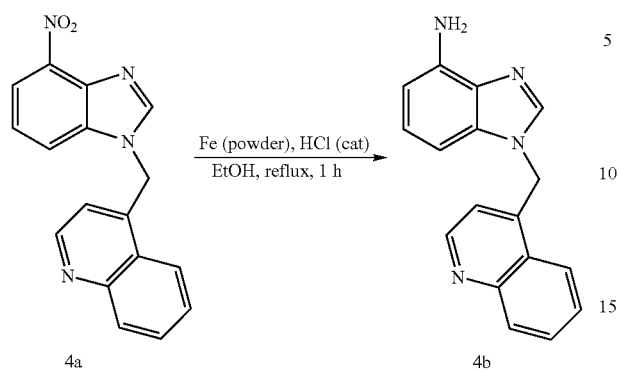

Compound 6 may be synthesized as illustrated by methods described in U.S. Pat. No. 5,212,182.

4-(4-Nitro-benzoimidazol-1-ylmethyl)-quinoline (4a)

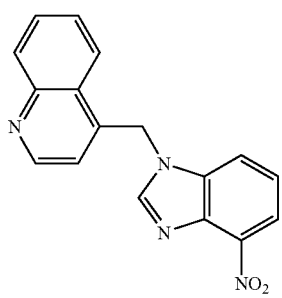

Compound 4a was synthesized in the same manner as compound 3c using 4-chloromethylquinoline hydrochloride instead of 4-chloromethylpyridine hydrochloride.

1-Quinolin-4-ylmethyl-1H-benzoimidazol-4-ylamine (4b)

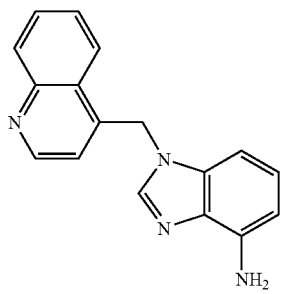

Compound 4b was synthesized in the same manner as compound 3d.

Example 6

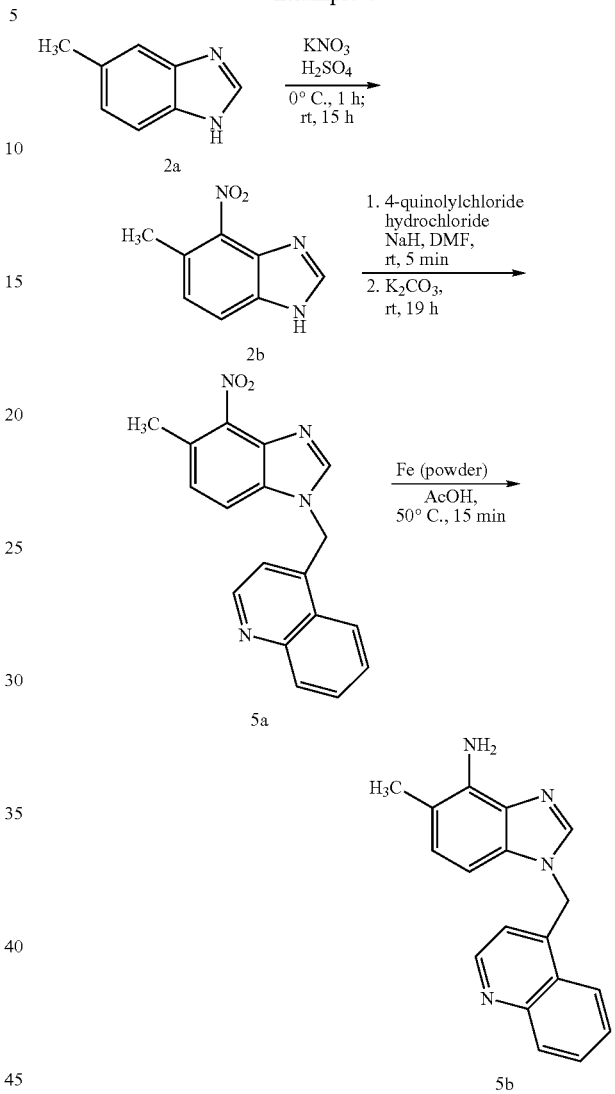

4-(5-Methyl-4-nitro-benzoimidazol-1-ylmethyl)-quinoline (5a)

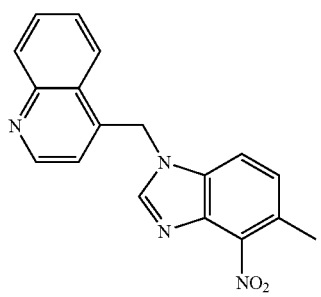

Compound 5a was synthesized in the same manner as compound 2c using 4-chloromethylquinoline hydrochloride instead of 4-chloromethylpyridine hydrochloride.

45

5-Methyl-1-quinolin-4-ylmethyl-1H-benzoimidazol-4-ylamine (5b)

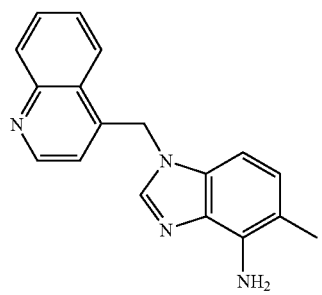

5b

Compound 5b was synthesized in the same manner as compound 2d.

1-(5-Bromo-2-methoxy-phenyl)-3-(1-quinolin-4-ylmethyl-1H-benzoimidazol-4-yl)-urea (2k)

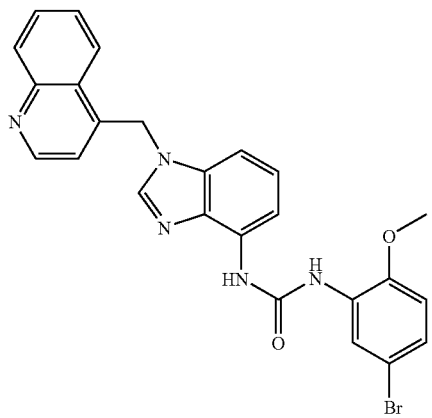

2k

To solution of compound 4b (50 mg, 0.2 mmol) in dichloromethane (3.0 mL) is added 0.04 g (0.2 mmol, 1 eq.) of 4-bromo-2-isocyanato-1-methoxy-benzene (40 mg, 0.2 mmol, 1 equiv.) and the resulting reaction mixture is heated to 40° C. for 2 hrs, then is cooled to room temperature and treated with ethyl ether. The precipitate is filtered and collected to give compound 2k as a white powder.

46

1-(5-Bromo-2-methoxy-phenyl)-3-(5-methyl-1-quinolin-4-ylmethyl-1H-benzoimidazol-4-yl)-urea (2l)

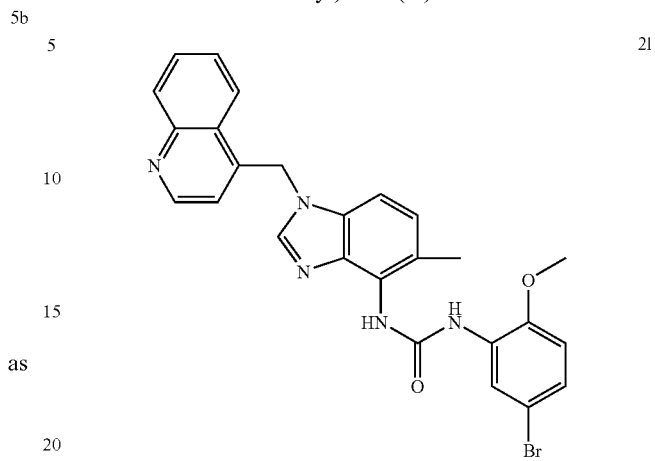

21

To solution of compound 5b (50 mg, 0.2 mmol) in dichloromethane (3.0 mL) is added (40 mg, 0.2 mmol, 1 equiv.) of 4-bromo-2-isocyanato-1-methoxy-benzene and the resulting reaction mixture is heated to 40° C. for 2 hrs, then is cooled to room temperature and treated with ethyl ether. The precipitate was filtered and collected to give compound 2l as a white powder.

Example 7

The following compounds were prepared using procedures similar to those described in Examples 3 to 6. Those of ordinary skill in the art of organic synthesis will recognize when starting materials or reaction conditions should be varied to obtain the desired compound.

MS data reported in this example was obtained as follows:

MS conditions: Electrospray MS is performed on a MICROMASS LCT equipped with a LockSpray source for accurate mass measurements. Spectra are acquired in positive ion mode from 100-1000 Da at an acquisition rate of 1 spectrum/ 0.9 s with a 0.1 s interscan delay. The instrument is tuned for a resolution of 5000 (FWHM). Every $5^{th}$ scan is taken from the reference position of the Lockspray source. Leucine enkephalin (556.2771 [M+H]$^+$) is used as the reference, or lock mass.

| Structure | Name/MW | M+ |
|---|---|---|
| 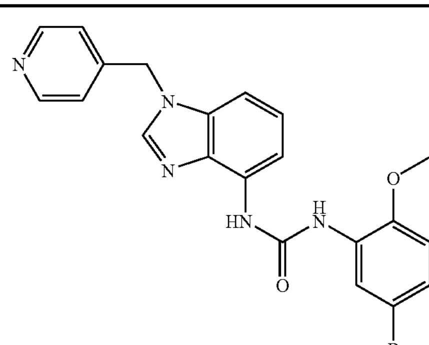 | 1-(5-Bromo-2-methoxy-phenyl)-3-(1-pyridin-4-ylmethyl-1H-benzoimidazol-4-yl)-urea<br>451.06 | 452.17 |

-continued

| Structure | Name/MW | M+ |
|---|---|---|
| | 1-(2-Methoxy-5-trifluoromethyl-phenyl)-3-(1-pyridin-4-ylmethyl-1H-benzoimidazol-4-yl)-urea<br>441.14 | 442.20 |
| | 1-(5-Bromo-2-methoxy-phenyl)-3-(1-quinolin-4-ylmethyl-1H-benzoimidazol-4-yl)-urea<br>501.08 | 502.03 |
| | 1-(5-Bromo-2-methoxy-phenyl)-3-(5-methyl-1-quinolin-4-ylmethyl-1H-benzoimidazol-4-yl)-urea<br>515.10 | 516.00 |
| | 1-(5-Bromo-2-methoxy-phenyl)-3-(5-methyl-1-pyridin-4-ylmethyl-1H-benzoimidazol-4-yl)-urea<br>455.16 | 456.05 |

-continued

| Structure | Name/MW | M+ |
|---|---|---|
| 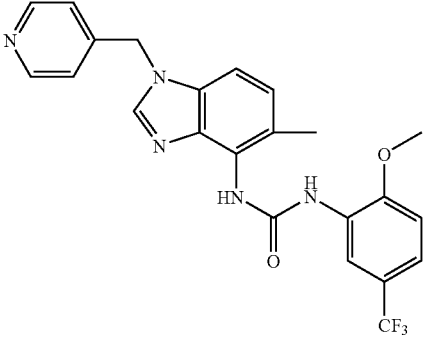 | 1-(2-Methoxy-5-trifluoromethyl-phenyl)-3-(5-methyl-1-pyridin-4-ylmethyl-1H-benzoimidazol-4-yl)-urea<br>465.08 | 466.04 |
| 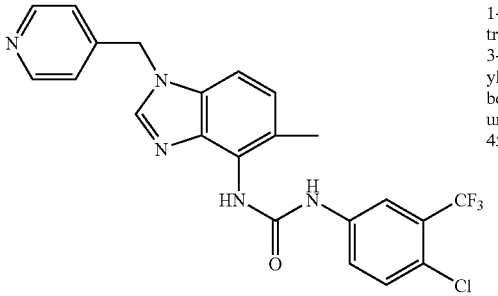 | 1-(4-Chloro-3-trifluoromethyl-phenyl)-3-(5-methyl-1-pyridin-4-ylmethyl-1H-benzoimidazol-4-yl)-urea<br>459.11 | 460.18 |
| 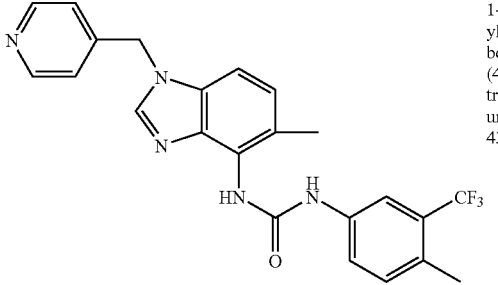 | 1-(5-Methyl-1-pyridin-4-ylmethyl-1H-benzoimidazol-4-yl)-3-(4-methyl-3-trifluoromethyl-phenyl)-urea<br>439.16 | 440.26 |

Example 8

Assay for EphB$_4$ Kinase Activity

The following is a procedure for a standard biochemical assay for EphB$_4$ Kinase Activity that can be used to test compounds disclosed in this application.

Materials:

96-well, ½ area flat bottom, white polystyrene plates are purchased from Costar, cat #3693.

The cytoplasmic domain of recombinant EphB$_4$ kinase (amino acids 596-987, *Homo sapiens* EphB$_4$, GENBANK Accession No. AY056047.1) with a C-terminal V5-(his)$_6$ tag is purified from Sf9 cells. Purity of >95% is assessed by Sypro-Ruby staining of SDS gels.

PTK Biotinylated Peptide Substrate 2, is purchased from Promega, cat #V288A.

LANCE Eu-W1024 labeled anti-phosphotyrosine antibody (PT66) is purchased from Perkin-Elmer, cat #AD0068. Kinase Buffer is purchased from Cell Signaling, cat #9802.

Dilutions of compounds are made in 100% DMSO at 20× the final desired concentration. Compounds in 100% DMSO are transferred (1.25 μL) to the 96 well assay plate. A 18.75 μL volume of master mix containing the final concentrations (in 25 ul) of 0.01% BSA, 1× Cell Signaling Kinase Buffer, 0.5 μM PTK Biotinylated Peptide Substrate 2, and 18.6 ng/well ng/well of EphB$_4$ kinase is added to all wells, except the four negative control wells (which contain no kinase), and mixed. To initiate the reaction, 5 μL of 550 uM ATP is added to each well. (Final Concentration of ATP=110 μM). The reactions are incubated for 1 hour at room temperature (RT). After incubation a quantity of 8.35 μL of a 4×SA-APC Detection Mix is added to each well. The final concentration of Eu-labelled PT66 antibody is 1 nM and the SA-APC is 20 nM (based on the SA moiety). The reaction plates are incubated at RT for at least 15 minutes after SA-APC Detection Mix addition. The reaction plates are read on an Envision plate reader (Perkin-Elmer) with 605 nm Excitation at 605 nm and 640 nm Emission wavelengths. Values are corrected for the fluorescence in the absence of enzyme and inhibition curves are fit to the data using a Logit curve-fitting algorithm. IC$_{50}$ values are determined from these inhibition curves.

Example 9

EphB4 Cellular Assay

The following is a procedure for a standard cell-based assay for EphB$_4$ kinase activity that can be used to test compounds disclosed in this application.

HEK293 cells stably expressing V5-epitope tagged EphB$_4$ are grown to ~75% confluency, and then incubated for 90 min at 37° C. in low serum media (Optimem) containing test compound. Cells are stimulated for 10 minutes at 37° C. with 500 ng/ml EphrinB$_2$/Fc chimera and 50 ng/ml goat-anti-human IgG (FC-specific) in low serum media containing test compound. Cells are washed in ice-cold PBS, lysed, and protein assays are performed on the cleared lysates. Equal protein amounts of each sample are subjected to SDS-PAGE and western blotting with either an anti-phosphotyrosine antibody or an anti-V5 antibody to control for total amounts of V5-epitope-tagged EphB$_4$ in each lysate.

Example 10

Biochemical Assay S

The following is a procedure for a standard biochemical assay that can be used to test activity of compounds disclosed herein as inhibitors of c-Kit, PDGFRβ, and VEGFR2, kinase activity.

Test compounds are diluted 1:20 from an original 200 μM DMSO stock and incubated with recombinant c-Kit (10 ng), or VEGFR2 (1 ng) enzyme (ProQinase GmbH, Germany), biotinylated peptide (PTK peptide 2, Promega) in Cell Signalling kinase buffer (c-Kit) or Upstate Kinase buffer (VEGFR2) and 5 ul of ATP (final concentrations: 85 μM for the VEGFR2 assay and 150 μM for the c-Kit assay) for 60 minutes at room temperature. For PDGFRβ, test compounds are diluted 1:20 from an original 200 μM DMSO stock and incubated with recombinant PDGFRβ (2 ng) (ProQinase GmbH, Germany), biotinylated peptide (PTK peptide 2, Promega), 1 μM poly-L-lysine (Sigma) in Upstate Kinase buffer and 5 μl of ATP (final concentration: 2.5 μM) for at least 15 minutes at room temperature. The final assay volume is 25 μl. After incubation a detection Mix, which includes 1 nM LANCE Eu-W1024 labeled anti-phosphotyrosine antibody PT66 (Perkin-Elmer, cat #AD0068) and 20 nM SA-APC (based on the SA moiety), is added. The reaction plates are incubated at room temperature for at least 15 minutes after SA-APC detection mix addition. The reaction plates are then read on an Envision plate reader (Perkin-Elmer) with 605 nm excitation 615 nM and 640 nm emission wavelengths.

For a negative control, i.e. a readout in which the kinases are not inhibited, the assay is run without any test compound added. Staurosporine, a general kinase inhibitor, is used as a positive control.

IC$_{50}$ values are determined from an 11-point saturation binding curve for test compounds that show significant inhibition of one of the tyrosine kinases. In these assays concentration of test compound ranges from 10 μM to 20 nM. Equilibrium binding parameters are determined by fitting the allosteric Hill equation to the measured values with the aid of the computer program, such as FitP™ (BIOSOFT, Ferguson, Mo.).

Example 11

Test Results

Certain compounds described in Examples 2 and 7 were tested in the assays for EphB$_4$ kinase activity (as outlined in Examples 8 and 9), and found to exhibit an IC$_{50}$ of 1 micromolar or less. Certain of those compounds exhibited an IC$_{50}$ of 500 nM or less in these assays.

Certain compounds of Examples 2 and 7 were tested in the assay for PDGFRβ kinase activity (as outlined in example 10), and found to exhibit an IC$_{50}$ of 1 micromolar or less. Certain of those compounds exhibited an IC$_{50}$ of 500 nM or less in the assay for PDGFRβ kinase activity.

Certain compounds described in Examples 2 and 7 were tested in the assay for c-Kit kinase activity (as outlined in example 10) and found to exhibit an IC$_{50}$ of 1 micromolar or less. Certain of those compounds exhibited an IC$_{50}$ of 500 nM or less in the assay for c-Kit kinase activity. Certain of those compounds exhibited an IC$_{50}$ of 50 nM or less in this assay.

Certain compounds described in Examples 2 and 7 were also tested in the assay for VEGFR2 kinase activity (as outlined in example 10). Certain of those compounds were found to exhibit an IC$_{50}$ of 1 micromolar or less. Certain of those compounds exhibited an IC$_{50}$ of 100 nM or less in this assay. Certain of those compounds exhibited an IC$_{50}$ of 50 nM or less in this assay.

Certain compounds described in Examples 2 and 7 were also tested in the assays described herein and were found to exhibit an IC$_{50}$ of 1 micromolar or less against two or more kinases chosen from EphB$_4$, PDGFRβ, c-Kit, and VEGFR2. Certain compounds described in Examples 2 and 7 were also tested in the assays described herein and were found to exhibit an IC$_{50}$ of 100 nm or less against two or more kinases chosen from EphB$_4$, PDGFRβ, c-Kit, and VEGFR2.

Certain compounds described in Examples 2 and 7 were also tested in the assays described herein and were found to exhibit an IC$_{50}$ of 1 micromolar or less against three or more kinases chosen from EphB$_4$, PDGFRβ, c-Kit, and VEGFR2. Certain compounds described in Examples 2 and 7 were also tested in the assays described herein and were found to exhibit an IC$_{50}$ of 100 nm or less against three or more kinases chosen from EphB$_4$, PDGFRβ, c-Kit, and VEGFR2.

Certain compounds described in Examples 2 and 7 were also tested in the assays described herein and were found to exhibit an IC$_{50}$ of 1 micromolar or less against each of EphB$_4$, PDGFRβ, c-Kit, and VEGFR2. Certain compounds described in Examples 2 and 7 were also tested in the assays described herein and were found to exhibit an IC$_{50}$ of 100 nm or less against each of EphB$_4$, PDGFRβ, c-Kit, and VEGFR2.

While certain embodiments have been shown and described, various modifications and substitutions may be made thereto without departing from the spirit and scope of the invention. Accordingly, it is to be understood that the present invention has been described by way of illustration and not limitations.

What is claimed is:

1. At least one chemical entity chosen from compounds of Formula 3

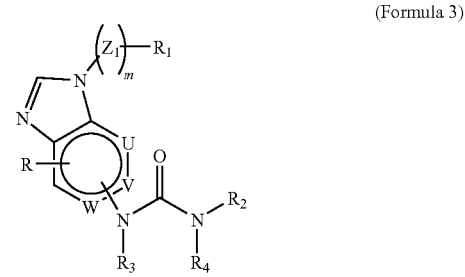

(Formula 3)

and pharmaceutically acceptable salts thereof, wherein
U, V, and W are CH;
R represents 0 to 2 substituents independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, sulfanyl, sulfinyl, sulfonyl, optionally substituted aryl, optionally substituted heteroaryl, and optionally substituted heterocycloalkyl;

$R_1$ is optionally substituted quinolin-4-yl;

$Z_1$ is —$CR_5R_6$— wherein each $R_5$ and $R_6$ is independently chosen from hydrogen, optionally substituted $C_1$-$C_6$ alkyl, and halo; and m is chosen from 0, 1, and 2;

$R_2$ is optionally substituted aryl; and $R_3$ and $R_4$ are each independently chosen from hydrogen, optionally substituted $C_1$-$C_6$ alkyl, optionally substituted aryl, and optionally substituted heteroaryl.

2. At least one chemical entity of claim 1 wherein at least one of $R_5$ and $R_6$ is hydrogen.

3. At least one chemical entity of claim 2 wherein both of $R_5$ and $R_6$ are hydrogen.

4. At least one chemical entity of claim 1 wherein m is 1 and at least one of $R_5$ and $R_6$ is hydrogen.

5. At least one chemical entity of claim 4 wherein both of $R_5$ and $R_6$ are hydrogen.

6. At least one chemical entity of claim 1 wherein m is 0.

7. At least one chemical entity of claim 1 wherein $R_2$ is chosen from phenyl, substituted phenyl,

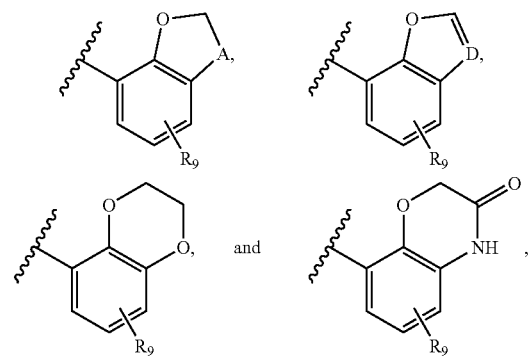

wherein

A is chosen from $CH_2$ and O,

D is chosen from CH and N, the wavy line represents the attachment point of $R_2$ to the urea group of Formula 1, and $R_9$ is chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, optionally substituted aryloxy, sulfanyl, sulfinyl, sulfonyl, optionally substituted aryl, optionally substituted heteroaryl, and optionally substituted heterocycloalkyl.

8. At least one chemical entity of claim 7 wherein $R_2$ is chosen from phenyl and substituted phenyl wherein substituted phenyl is chosen from mono-, di-, and tri-substituted phenyls and wherein substituents on the substituted phenyl are independently chosen from hydroxy, nitro, cyano, optionally substituted amino, aminocarbonyl, halo, carboxy, optionally substituted acyl, optionally substituted alkoxycarbonyl, optionally substituted $C_1$-$C_6$ alkyl, optionally substituted $C_1$-$C_6$ alkoxy, optionally substituted aryloxy, sulfanyl, sulfinyl, sulfonyl, optionally substituted aryl, optionally substituted heteroaryl, and optionally substituted heterocycloalkyl.

9. At least one chemical entity of claim 8 wherein the substituents on the substituted phenyl are independently chosen from hydroxy, nitro, cyano, optionally substituted amino, halo, carboxy, optionally substituted $C_1$-$C_6$ alkyl, optionally substituted $C_1$-$C_6$ alkoxy, optionally substituted phenoxy, $C_1$-$C_6$ alkylsulfanyl, $C_1$-$C_6$ acyl, $C_1$-$C_6$ alkoxycarbonyl, optionally substituted heteroaryl, and optionally substituted heterocycloalkyl.

10. At least one chemical entity of claim 9 wherein the substituents on the substituted phenyl are independently chosen from hydroxy, cyano, halo, optionally substituted $C_1$-$C_2$ alkyl, phenoxy, and optionally substituted $C_1$-$C_2$ alkoxy.

11. At least one chemical entity of claim 10 wherein the substituents on the substituted phenyl are independently chosen from halo, methyl, methoxy, ethoxy, and trifluoromethyl.

12. At least one chemical entity of claim 1 wherein R represents 1 or 2 substituents independently chosen from halo, $C_1$-$C_2$ alkyl, and $C_1$-$C_2$ alkoxy.

13. At least one chemical entity of claim 12 wherein R represents 1 or 2 substituents independently chosen from halo, methyl, and methoxy.

14. At least one chemical entity of claim 13 wherein R represents a substituent chosen from halo, methyl, and methoxy.

15. At least one chemical entity of claim 1 wherein R is absent.

16. At least one chemical entity of claim 1 wherein $R_3$ and $R_4$ are each independently chosen from hydrogen and methyl.

17. At least one chemical entity of claim 16 wherein $R_3$ and $R_4$ are hydrogen.

18. At least one chemical entity according to claim 1, wherein the at least one chemical entity exhibits an $IC_{50}$ of 1 micromolar or less in a standard in vitro assay of $EphB_4$ kinase activity.

19. At least one chemical entity according to claim 18, wherein the at least one chemical entity exhibits an $IC_{50}$ of 500 nanomolar or less in a standard in vitro assay of $EphB_4$ kinase activity.

20. At least one chemical entity according to claim 1, wherein the at least one chemical entity exhibits an $IC_{50}$ of 1 micromolar or less in a standard in vitro assay of PDGFRβ kinase activity.

21. At least one chemical entity according to claim 20, wherein the at least one chemical entity exhibits an $IC_{50}$ of 500 nanomolar or less in a standard in vitro assay of PDGFRβ kinase activity.

22. At least one chemical entity according to claim 1, wherein the at least one chemical entity exhibits an $IC_{50}$ of 1 micromolar or less in a standard in vitro assay of c-Kit kinase activity.

23. At least one chemical entity according to claim 22, wherein the at least one chemical entity exhibits an $IC_{50}$ of 500 nanomolar or less in a standard in vitro assay of c-Kit kinase activity.

24. At least one chemical entity according to claim 23, wherein the at least one chemical entity exhibits an $IC_{50}$ of 50 nanomolar or less in a standard in vitro assay of c-Kit kinase activity.

25. At least one chemical entity according to claim 1, wherein the at least one chemical entity exhibits an $IC_{50}$ of 1 micromolar or less in a standard in vitro assay of VEGFR2 kinase activity.

26. At least one chemical entity according to claim 25 wherein the at least one chemical entity exhibits an $IC_{50}$ of 500 nM or less in a standard in vitro assay of VEGFR2 kinase activity.

27. At least one chemical entity according to claim 26 wherein the at least one chemical entity exhibits an $IC_{50}$ of 50 nM or less in a standard in vitro assay of VEGFR2 kinase activity.

28. At least one chemical entity of claim 1 wherein the compound of Formula 3 is chosen from
- 1-(5-Bromo-2-methoxy-phenyl)-3-(1-quinolin-4-ylmethyl-1H-benzoimidazol-4-yl)-urea;
- 1-(5-Bromo-2-methoxy-phenyl)-3-(5-methyl-1-quinolin-4-ylmethyl-1H-benzoimidazol-4-yl)-urea.

29. A pharmaceutical composition, comprising at least one chemical entity of claim 1, together with at least one pharmaceutically acceptable vehicle chosen from carriers, adjuvants, and excipients.

30. A pharmaceutical composition of claim 29, wherein the composition is formulated in a form chosen from injectable fluids, aerosols, creams, gels, tablets, pills, capsules, syrups, ophthalmic solutions, and transdermal patches.

* * * * *